US007205137B2

(12) United States Patent
Glössl et al.

(10) Patent No.: US 7,205,137 B2
(45) Date of Patent: Apr. 17, 2007

(54) β1,2-XYLOSYLTRANSFERASE-GENE FROM ARABIDOPSIS

(76) Inventors: Josef Glössl, Ameisgasse 63/4/19, A-1140 Vienna (AT); Richard Strasser, Rudolf Bärenhartgasse 15/6, A-1170 Vienna (AT); Jan Mucha, S. Kralika 89, SK-841 00 Bratislava (SK); Lukas Mach, Lerchenfelder Strasse 9-11/2/41, A-1070 Vienna (AT); Friedrich Altmann, Linzerstrasse 412/7/5, A-1140 Vienna (AT); Iain B. Wilson, Antonigasse 92/3, A-1180 Vienna (AT); Herta Steinkellner, Bauernfeldgasse 9/2/3, A-1190 Vienna (AT)

( * ) Notice: Subject to any disclaimer, the term of this patent is extended or adjusted under 35 U.S.C. 154(b) by 431 days.

(21) Appl. No.: 10/220,467

(22) PCT Filed: Mar. 2, 2001

(86) PCT No.: PCT/EP01/02352

§ 371 (c)(1),
(2), (4) Date: Mar. 7, 2003

(87) PCT Pub. No.: WO01/64901

PCT Pub. Date: Sep. 7, 2001

(65) Prior Publication Data

US 2004/0121325 A1 Jun. 24, 2004

(30) Foreign Application Priority Data

Mar. 3, 2000 (AT) .............................. A 355/2000

(51) Int. Cl.
*C07H 21/04* (2006.01)
*A01H 5/00* (2006.01)
*C12N 9/10* (2006.01)
*C12Q 1/68* (2006.01)

(52) U.S. Cl. ......................... 435/193; 435/6; 435/69.1; 435/320.1; 435/183; 536/23.2

(58) Field of Classification Search .................... 435/6, 435/69.1
See application file for complete search history.

(56) References Cited

U.S. PATENT DOCUMENTS

2001/0016344 A1* 8/2001 Elbein et al. ............... 435/193

FOREIGN PATENT DOCUMENTS

| | | |
|---|---|---|
| EP | 1 033405 A2 * | 9/2000 |
| EP | 1033405 | 9/2002 |
| WO | WO 99/29835 | 6/1999 |
| WO | WO 01/29242 | 4/2001 |

OTHER PUBLICATIONS

Martin et al. Plant Physiol. 1999. vol. 120, pp. 553-557.*

Burke, "Clearing the way for ribozymes," *Nature Biotechnology*, 15:414-415, 1997.

Chen et al., "Efficient hammerhead ribozyme and antisense RNA targeting in a slow ribosome *Escherichia coli* mutant," *Nature Biotechnology*, 15:432-435, 1997.

EMBL Database Accession No. AB015479.

EMBL Database Accession No. AI994524.

EMBL Database Accession No. ATH277603.

Jenkins et al., "Getting the glycosylation right: implications for the biotechnology industry," *Nature Biotechnology*, 14:975-981, 1996.

Kuwabara et al., "Formation of a catalytically active dimer by tRNA $^{Val}$ —driven short ribozymes," *Nature Biotechnology*, 116:961-964, 1998.

Lerouge et al., "N-Glycoprotein biosynthesis in plants: recent developments and future trends," *Plant Mol. Biol.*, 38:31-48, 1998.

Patzel and Sczakiel, "Theoretical design of antisense RNA structures substantially improves annealing kinetics and efficacy in human cells," *Nature Biotechnology*, 16:64-68, 1998.

Pooga et al., "PNA oligomers as tools for specific modulation of gene expression," *Bimolecular Engineering*, 17:183-192, 2001.

Ruan et al., "Towards Arabidopsis genome analysis: monitoring expression profiles of 1400 genes using cDNA microarrays," *The Plant Journal*, 15:821-833, 1998.

Schaefer and Zryd, "Efficient gene targeting in the moss Physcomitrella patens," *Plant J.*, 11(6):1195-1206, 1997.

Staudacher and Marz, "Strict order of (Fuc to Asn-linked GlCNAc) fucosyltransferases forming core-difucosylated structures," *Glycoconjugate Journal*, 15:355-360, 1998.

Staudacher et al., "Functional purification and characterization of a GDP-fucose: β-N-acetylglucosamine (Fuc to Asn linked GlcNAc) α1,3-fucosyltransferase form mung beans," *Glycoconjugate Journal*, 12:780-786, 1995.

Strasser et al., "Molecular cloning and characterization of a cDNA coding for β1,2N-acetylglucosaminyltransferase I (GlcNAc-TI) from Nicotiana tabacum," *Glycobiology*, 9:779-785, 1999.

von Schaewen, "Isolation of a mutant Arabidopsis plant that lacks N-Acetyle glucosaminyl transferase I and is unable to synthesize golgi-modified complex N-linked glycans[1,2] ," *Plant Physiol.*, 102:1109-1118, 1993.

Wilson et al., "Core α1,3-fucose is a key part of the epitope recognized by antibodies reacting against plant N-linked oligosaccharides and is present in a wide variety of plant extracts," *Glycobiology*, 8:651-661, 1998.

Zeng et al., "Purification and specificity of β1,2-Xylosyltransferase, an enzyme that contributes to the allergenicity of some plant proteins," *J. Biol. Chem.*, 272:31340-31347, 1997.

* cited by examiner

*Primary Examiner*—Tekchand Saidha
*Assistant Examiner*—Md. Y. Meah
(74) *Attorney, Agent, or Firm*—Fulbright & Jaworski LLP

(57) ABSTRACT

A DNA molecule is provided which comprises a sequence according to SEQ ID NO: 8 having an open reading frame from base pair 227 to base pair 1831 or having at least 50% homology to the above-indicated sequence, or hybridizing with the above-indicated sequence under stringent conditions, or comprising a sequence which has degenerated to the above-indicated DNA sequence because of the genetic code, the sequence coding for a plant protein having β1,2-xylosyltransferase activity or being complementary thereto.

10 Claims, 13 Drawing Sheets

| | |
|---|---|
| Peptide 3 from patent WO9929835A1 | SQVQAIHDASVIIGAHGAGLTHIVSAL |
| Peptide 2 from patent WO9929835A1[1] | GLEYHAIN |

```
Soybean:      SQVQAIHDASVIIGAHGAGLTHIVSAL-------------------------------------GLEYHAIN
               QV  AI  DASVIIGAHGAGLTHIVSA                                   GLEYHA
A.thaliana:   DQVRAIQDASVIIGAHGAGLTHIVSATPNTTIFEIISVEFQRPHFELIAKWKGLEYHAMH
```

| | |
|---|---|
| Primer 1 | 5′-ATGAGTAAACGGAATCCGAAG-3′ |
| Primer 2 | 5′-TTAGCAGCCAAGGCTCTTCAT-3′ |
| Primer 3 | 5′-GATCAAGTCCGAGCCATTCAA-3′ |
| Primer 4 | 5′-CGCGTGATACTCCAATCCTTT-3′ |

[1]The C-terminal amino acids LG were omitted

Fig. 1

```
                    AAATCTGCAGACTCTCAAAATTCCGATTCATCTTATTGAAGAACAA   46
TTTTCCGGCGAAACAGCCGATGAAGTCTCGCCTGAATCTTCTGTACCTTTCACCGGCGAT  106
TGACTTCACTTCAGAATCGAGAGAGAAGAAATCGATGGAAAACTAAAAATAGAAAGAGTT  166
TCAAATTCTCGCTCTCTCTTCAAAACCGCAAATCAAGGGAACGAGAGACGAGAGAGAGAG  226

ATGAGTAAACGGAATCCGAAGATTCTGAAGATTTTTCTGTATATGTTACTTCTCAACTCT  286

CTCTTTCTCATCATCTACTTCGTTTTTCACTCATCGTCGTTTTCACCGGAGCAGTCACAG  346

CCTCCTCATATATACCACGTTTCAGTGAATAACCAATCGGCGATTCAGAAACCGTGGCCG  406

ATCTTACCTTCTTACCTCCCATGGACGCCGCCGCAGAGGAATCTACCAACTGGCTCCTGC  466

GAAGGTTACTTCGGGAATGGATTTACAAAGAGAGTTGACTTCCTTAAGCCGAGGATTGGA  526

GGAGGAGGAGAAGGAAGCTGGTTCCGATGTTTTTACAGTGAGACATTACAGAGTTCGATT  586

TGTGAAGGAAGGAATCTGAGAATGGTTCCGGATCGGATTGTTATGTCGAGAGGAGGTGAG  646

AAGTTAGAGGAAGTTATGGGGAGGAAAGAGGAGGAGGAGCTTCCTGCGTTTCGACAAGGT  706

GCGTTTGAGGTAGCGGAAGAGGTTTCTTCACGGTTAGGTTTTAAGAGACACCGTCGTTTT  766

GGTGGAGGAGAAGGAGGTAGTGCGGTTTCTCGGCGGCTGGTGAATGATGAGATGTTGAAT  826

GAATATATGCAAGAAGGTGGAATTGATAGACATACAATGAGAGATTTGGTTGCTTCGATT  886

CGTGCTGTTGATACCAATGATTTCGTTTGTGAAGAGTGGGTGGAGGAACCGACCTTGCTT  946

GTCACTAGATTCGAGTACGCAAATCTCTTCCATACTGTGACAGATTGGTATAGTGCCTAT 1006

GTTTCGTCTAGAGTCACCGGTTTGCCTAATCGACCTCACGTTGTTTTCGTTGACGGACAC 1066

TGCACGACGCAGCTAGAAGAAACATGGACAGCTTTGTTTTCCGGAATCAGATACGCAAAG 1126

AACTTCACCAAACCGGTTTGTTTCCGCCACGCGATTCTTTCACCATTGGGATACGAAACC 1186

GCTCTTTTTAAAGGCTTGTCCGGAGAAATAGACTGCAAGGGAGATTCAGCTCACAATCTG 1246

TGGCAAAACCCGGACGATAAAAGGACTGCGAGGATATCAGAGTTTGGTGAAATGATCAGA 1306

GCAGCTTTCGGGTTGCCTGTCAATAGACACCGCTCATTAGAAAAGCCGCTATCATCATCA 1366

TCATCATCAGCCTCAGTTTATAATGTTCTTTTTGTCCGCCGTGAAGATTACTTAGCCCAT 1426

CCTCGTCATGGCGGTAAAGTCCAGTCTCGGCTCATCAATGAGGAAGAAGTGTTCGACTCG 1486

TTGCATCATTGGGTTGCAACTGGGTCCACCGGTCTGACCAAATGCGGGATTAACCTTGTG 1546

AATGGCTTGCTTGCACACATGTCAATGAAAGATCAAGTCCGAGCCATTCAAGATGCTTCA 1606

GTGATCATAGGAGCTCATGGAGCAGGACTGACTCACATTGTCTCTGCAACACCAAACACA 1666

ACGATATTTGAGATAATAAGCGTCGAGTTTCAGAGACCTCATTTCGAGCTTATAGCTAAG 1726

TGGAAAGGATTGGAGTATCACGCGATGCATCTGGCGAACTCACGAGCGGAACCAACGGCT 1786

GTGATTGAGAAGTTAACGGAGATCATGAAGAGCCTTGGCTGCTAA 1831
```

Fig. 2

```
        10         20         30         40         50         60
MSKRNPKILKIFLYMLLLNSLFLIIYFVFHSSSFSPEQSQPPHIYHVSVNNQSAIQKPWP

        70         80         90        100        110        120
ILPSYLPWTPPQRNLPTGSCEGYFGNGFTKRVDFLKPRIGGGGEGSWFRCFYSETLQSSI

       130        140        150        160        170        180
CEGRNLRMVPDRIVMSRGGEKLEEVMGRKEEEELPAFRQGAFEVAEEVSSRLGFKRHRRF

       190        200        210        220        230        240
GGGEGGSAVSRRLVNDEMLNEYMQEGGIDRHTMRDLVASIRAVDTNDFVCEEWVEEPTLL

       250        260        270        280        290        300
VTRFEYANLFHTVTDWYSAYVSSRVTGLPNRPHVVFVDGHCTTQLEETWTALFSGIRYAK

       310        320        330        340        350        360
NFTKPVCFRHAILSPLGYETALFKGLSGEIDCKGDSAHNLWQNPDDKRTARISEFGEMIR

       370        380        390        400        410        420
AAFGLPVNRHRSLEKPLSSSSSSASVYNVLFVRREDYLAHPRHGGKVQSRLINEEEVFDS

       430        440        450        460        470        480
LHHWVATGSTGLTKCGINLVNGLLAHMSMKDQVRAIQDASVIIGAHGAGLTHIVSATPNT

       490        500        510        520        530
TIFEIISVEFQRPHFELIAKWKGLEYHAMHLANSRAEPTAVIEKLTEIMKSLGC
```

Fig. 3

```
xt-Ath6.seq   : ATGAGTAAACGGAATCCGAAGATTCTGAAGATTTTTCTGTATATGTTACTTCTCAACTCTCTCTTTCTCATCATCTACTT :  80
xt-Ath9.seq   : ................................................................................ :  80
xt-Ath16.seq  : ................................................................................ :  80
xt-Athgen.seq : ................................................................................ :  80
xt-AthEST.seq : -------------------------------------------------------------------------------- :   -

xt-Ath6.seq   : CGTTTTTCACTCATCGTCGTTTTCACCGGAGCAGTCACAGCCTCCTCATATATACCACGTTTCAGTGAATAACCAATCGG : 160
xt-Ath9.seq   : ............................................................A................... : 160
xt-Ath16.seq  : ................................................................................ : 160
xt-Athgen.seq : ................................................................................ : 160
xt-AthEST.seq : -------------------------------------------------------------------------------- :   -

xt-Ath6.seq   : CGATTCAGAAACCGTGGCCGATCTTACCTTCTTACCTCCCATGGACGCCGCCGCAGAGGAATCTACCAACTGGCTCCTGC : 240
xt-Ath9.seq   : ................................................................................ : 240
xt-Ath16.seq  : ................................................................................ : 240
xt-Athgen.seq : ................................................................................ : 240
xt-AthEST.seq : -------------------------------------------------------------------------------- :   -

xt-Ath6.seq   : GAAGGTTACTTCGGGAATGGATTTACAAAGAGAGTTGACTTCCTTAAGCCGAGGATTGGAGGAGGAGGAGAAGGAAGCTG : 320
xt-Ath9.seq   : ................................................................................ : 320
xt-Ath16.seq  : .................................................T.............................. : 320
xt-Athgen.seq : ................................................................................ : 320
xt-AthEST.seq : -------------------------------------------------------------------------------- :   -

xt-Ath6.seq   : GTTCCGATGTTTTTACAGTGAGACATTACAGAGTTCGATTTGTGAAGGAACGAATCTGAGAATGGTTCCGGATCGGATTG : 400
xt-Ath9.seq   : ................................................................................ : 400
xt-Ath16.seq  : ................................................................................ : 400
xt-Athgen.seq : ................................................................................ : 400
xt-AthEST.seq : -------------------------------------------------------------------------------- :   -

xt-Ath6.seq   : TTATGTCGAGAGGAGGTGAGAAGTTAGAGGAAGTTATGGGGAGGAAAGAGGAGGAGGAGCTTCCTGCGTTTCGACAAGGT : 480
xt-Ath9.seq   : ................................................................................ : 480
xt-Ath16.seq  : ..........................A..................................................... : 480
xt-Athgen.seq : ................................................................................ : 480
xt-AthEST.seq : -------------------------------------------------------------------------------- :   -

xt-Ath6.seq   : GCGTTTGAGGTAGCGGAAGAGGTTTCTTCACGGTTAGGTTTTAAGAGACACCGTCGTTTTGGTGGAGGAGAAGGAGGTAG : 560
xt-Ath9.seq   : ................................................................................ : 560
xt-Ath16.seq  : ................................................................................ : 560
xt-Athgen.seq : ................................................................................ : 560
xt-AthEST.seq : -------------------------------------------------------------------------------- :   -
```

Fig. 4a

```
xt-Ath6.seq   : TGCGGTTTCTCGGCGGCTGGTGAATGATGAGATGTTGAATGAATATATGCAAGAAGGTGGAATTGATAGACATACAATGA :  640
xt-Ath9.seq   : ................................................................................ :  640
xt-Ath16.seq  : .......................................C........................................ :  640
xt-Athgen.seq : ................................................................................ :  640
xt-AthEST.seq : -------------------------------------------------------------------------------- :

xt-Ath6.seq   : GAGATTTGGTTGCTTCGATTCGTGCTGTTGATACCAATGATTTCGTTTGTGAAGAGTGGGTGGAGGAACCGACCTTGCTT :  720
xt-Ath9.seq   : ................................................................................ :  720
xt-Ath16.seq  : ................................................................................ :  720
xt-Athgen.seq : ................................................................................ :  720
xt-AthEST.seq : --------........................................................................ :   72

xt-Ath6.seq   : GTCACTAGATTCGAGTACGCAAATCTCTTCCATACTGTGACAGATTGGTATAGTGCCTATGTTTCGTCTAGAGTCACCGG :  800
xt-Ath9.seq   : ................................................................................ :  800
xt-Ath16.seq  : ......................................................................A......... :  800
xt-Athgen.seq : ................................................................................ :  800
xt-AthEST.seq : ................................................................................ :  152

xt-Ath6.seq   : TTTGCCTAATCGACCTCACGTTGTTTTCGTTGACGGACACTGCACGACGCAGCTAGAAGAAACATGGACAGCTTTGTTTT :  880
xt-Ath9.seq   : ................................................................................ :  880
xt-Ath16.seq  : ................................................................................ :  880
xt-Athgen.seq : ................................................................................ :  880
xt-AthEST.seq : ................................................................................ :  232

xt-Ath6.seq   : CCGGAATCAGATACGCAAAGAACTTCACCAAACCGGTTTGTTTCCGCCACGCGATTCTTTCACCATTGGGATACGAAACC :  960
xt-Ath9.seq   : ..................................................A............................. :  960
xt-Ath16.seq  : .............................G.................................................. :  960
xt-Athgen.seq : ................................................................................ :  960
xt-AthEST.seq : ................................................................................ :  312

xt-Ath6.seq   : GCTCTTTTTAAAGGCTTGTCCGGAGAAATAGACTGCAAGGGAGATTCAGCTCACAATCTGTGGCAAAACCCGGACGATAA : 1040
xt-Ath9.seq   : .....................................G.......................................... : 1040
xt-Ath16.seq  : ................................................................................ : 1040
xt-Athgen.seq : ................................................................................ : 1040
xt-AthEST.seq : ................................C............................................... :  392

xt-Ath6.seq   : AAGGACTGCGAGGATATCAGAGTTTGGTGAAATGATCAGAGCAGCTTTCGGGTTGCCTGTCAATAGACACCGCTCATTAG : 1120
xt-Ath9.seq   : ................................................................................ : 1120
xt-Ath16.seq  : ................................................................................ : 1120
xt-Athgen.seq : ................................................................................ : 1120
xt-AthEST.seq : ........................C....G............................GTC....TA............C :  472
```

Fig. 4b

```
xt-Ath6.seq   : AAAAGCCGCTATCATCATCATCATCATCAGCCTCAGTTTATAATGTTCTTTTTGTCCGCCGTGAAGATTACTTAGCCCAT : 1200
xt-Ath9.seq   : .........................G...................................................... : 1200
xt-Ath16.seq  : ................................................................................ : 1200
xt-Athgen.seq : ................................................................................ : 1200
xt-AthEST.seq : G........----------------------------------------------------------------------- :  482

xt-Ath6.seq   : CCTCGTCATGGCGGTAAAGTCCAGTCTCGGCTCATCAATGAGGAAGAAGTGTTCGACTCGTTGCATCATTGGGTTGCAAC : 1280
xt-Ath9.seq   : ................................................................................ : 1280
xt-Ath16.seq  : ................................................................................ : 1280
xt-Athgen.seq : ................................................................................ : 1280
xt-AthEST.seq : -------------------------------------------------------------------------------- :    -

xt-Ath6.seq   : TGGGTCCACCGGTCTGACCAAATGCGGGATTAACCTTGTGAATGGCTTGCTTGCACACATGTCAATGAAAGATCAAGTCC : 1360
xt-Ath9.seq   : ................................................................................ : 1360
xt-Ath16.seq  : ................................................................................ : 1360
xt-Athgen.seq : ................................................................................ : 1360
xt-AthEST.seq : -------------------------------------------------------------------------------- :    -

xt-Ath6.seq   : GAGCCATTCAAGATGCTTCAGTGATCATAGGAGCTCATGGAGCAGGACTGACTCACATTGTCTCTGCAACACCAAACACA : 1440
xt-Ath9.seq   : ................................................................................ : 1440
xt-Ath16.seq  : ................................................................................ : 1440
xt-Athgen.seq : ................................................................................ : 1440
xt-AthEST.seq : -------------------------------------------------------------------------------- :    -

xt-Ath6.seq   : ACGATATTTGAGATAATAAGCGTCGAGTTTCAGAGACCTCATTTCGAGCTTATAGCTAAGTGGAAAGGATTGGAGTATCA : 1520
xt-Ath9.seq   : ................................................................................ : 1520
xt-Ath16.seq  : ................................................................................ : 1520
xt-Athgen.seq : ................................................................................ : 1520
xt-AthEST.seq : -------------------------------------------------------------------------------- :    -

xt-Ath6.seq   : CGCGATGCATCTGGCGAACTCACGAGCGGAACCAACGGCTGTGATTGAGAAGTTAACGGAGATCATGAAGAGCCTTGGCT : 1600
xt-Ath9.seq   : ................................................................................ : 1600
xt-Ath16.seq  : .....................G.......................................................... : 1600
xt-Athgen.seq : ................................................................................ : 1600
xt-AthEST.seq : -------------------------------------------------------------------------------- :    -

xt-Ath6.seq   : GCTAA : 1605
xt-Ath9.seq   : ..... : 1605
xt-Ath16.seq  : ..... : 1605
xt-Athgen.seq : ..... : 1605
xt-AthEST.seq : ----- :    -
```

Fig. 4c

```
xt-Ath6.seq   : MSKRNPKILKIFLYMLLLNSLFLIIYFVFHSSSFSPEQSQPPHIYHVSVNNQSAIQKPWPILPSYLPWTPPQRNLPTGSC :  80
xt-Ath9.seq   : ................................................................................ :  80
xt-Ath16.seq  : ................................................................................ :  80
xt-Athgen.seq : ................................................................................ :  80
xt-AthEST.seq : -------------------------------------------------------------------------------- :   -

xt-Ath6.seq   : EGYFGNGFTKRVDFLKPRIGGGGEGSWFRCFYSETLQSSICEGRNLRMVPDRIVMSRGGEKLEEVMGRKEEEELPAFRQG : 160
xt-Ath9.seq   : ................................................................................ : 160
xt-Ath16.seq  : ................L.............................................K................. : 160
xt-Athgen.seq : ................................................................................ : 160
xt-AthEST.seq : -------------------------------------------------------------------------------- :   -

xt-Ath6.seq   : AFEVAEEVSSRLGFKRHRRFGGGEGGSAVSRRLVNDEMLNEYMQEGGIDRHTMRDLVASIRAVDTNDFVCEEWVEEPTLL : 240
xt-Ath9.seq   : ................................................................................ : 240
xt-Ath16.seq  : ................................................................................ : 240
xt-Athgen.seq : ................................................................................ : 240
xt-AthEST.seq : --------------------------------------------------------........................ :  24

xt-Ath6.seq   : VTRFEYANLFHTVTDWYSAYVSSRVTGLPNRPHVVFVDGHCTTQLEETWTALFSGIRYAKNFTKPVCFRHAILSPLGYET : 320
xt-Ath9.seq   : ......................................................................T......... : 320
xt-Ath16.seq  : .......................K.......................................R................ : 320
xt-Athgen.seq : ................................................................................ : 320
xt-AthEST.seq : ................................................................................ : 104

xt-Ath6.seq   : ALFKGLSGEIDCKGDSAHNLWQNPDDKRTARISEFGEMIRAAFGLPVNRHRSLEKPLSSSSSSASVYNVLFVRREDYLAH : 400
xt-Ath9.seq   : ............R................................................................... : 400
xt-Ath16.seq  : ................................................................................ : 400
xt-Athgen.seq : ................................................................................ : 400
xt-AthEST.seq : ...........R.......................R.........GHSN....R..------------------------ : 160

xt-Ath6.seq   : PRHGGKVQSRLINEEEVFDSLHHWVATGSTGLTKCGINLVNGLLAHMSMKDQVRAIQDASVIIGAHGAGLTHIVSATPNT : 480
xt-Ath9.seq   : ................................................................................ : 480
xt-Ath16.seq  : ................................................................................ : 480
xt-Athgen.seq : ................................................................................ : 480
xt-AthEST.seq : -------------------------------------------------------------------------------- :   -

xt-Ath6.seq   : TIFEIISVEFQRPHFELIAKWKGLEYHAMHLANSRAEPTAVIEKLTEIMKSLGC : 534
xt-Ath9.seq   : ...................................................... : 534
xt-Ath16.seq  : ...................................................... : 534
xt-Athgen.seq : ...................................................... : 534
xt-AthEST.seq : ------------------------------------------------------ :   -
```

Fig. 5

GnGn

GnGnX

```
soybean     : RXXXXXXXXXXXXXXXXXXXXXXXXXXXXXXXXXXXXXXXXXXXXXXXXXXXXXXXXXXXXXXXXXXXXXXXXXXXXXXXX :  81
A.thaliana  : MSKRNPKILKIFLYMLLLNSLFLIIYFVFHSSSFSPEQSQPPHIYHVSVNNQSAIQKPWPILPSYLPWTPPQRNLPTGSCE :  81

soybean     : XXXXXXXXXXXXXXXXXXXXXXXXXXXXXXXXXXXXXXXXXXXXXXXXXXXXXXXXXXXXXXXXXXXXXXXXXXXXXXXXX : 162
A.thaliana  : GYFGNGFTKRVDFLKPRIGGGGEGSWFRCFYSETLQSSICEGRNLRMVPDRIVMSRGGEKLEEVMGRKEEEELPAFRQGAF : 162

soybean     : XXXXXXXXXXXXXXXXXXSG-PRXXXXXXXXXXXXLDEYVPRGGIDRHTMRDLIAKIRIVRGKDEQCDEWIEEPTLLVTR : 242
A.thaliana  : EVAEEVSSRLGFKRHRRFGGEGGSAVSRRLVNDEMLNEYMQEGGIDRHTMRDLVASIRAVDTNDFVCEEWVEEPTLLVTR : 243

soybean     : FEYANLFHTVTDWYSAYVSSRVTALPNRPHVIFVDGHCKAPLEETWKALFSSVGYAKSFSGSVCFHHAILSPLGYETAMFR : 323
A.thaliana  : FEYANLFHTVTDWYSAYVSSRVTGLPNRPHVVFVDGHCTTQLEETWTALFSGIRYAKNFTKPVCFRHAILSPLGYETALFK : 324

soybean     : GLSEHIDCYGAPAQELLQNLNDHKTARLSEFGEMVRAAFGLPLNVNHXMEXXXXXXXXPLAGHNVLFVRREDYLAHPRHSG : 404
A.thaliana  : GLSGEIDCKGDSAHNLWQNPDDKRTARISEFGEMIRAAFGLPVNRHRSLEKPLSSSSSSASVYNVLFVRREDYLAHPRHGG : 405

soybean     : KLESRLSNEQEVFNSLKSWXXXXXSNYKGCKINLVNGLFAHMSMKDQVQAIHDASVIIGAHGAG----------------- : 468
A.thaliana  : KVQSRLINEEEVFDSLHHWVATGSTGLTKCGINLVNGLLAHMSMKDQVRAIQDASVIIGAHGAGLTHIVSATPNTTIFEII : 486

soybean     : ------------------------------------------------- :   -
A.thaliana  : SVEFQRPHFELIAKWKGLEYHAMHLANSRAEPTAVIEKLTEIMKSLGC- : 534
```

Fig. 11

β1,2-XYLOSYLTRANSFERASE-GENE FROM ARABIDOPSIS

The invention relates to polynucleotides coding for a β1,2-xylosyltransferase. Furthermore, the invention relates to vectors comprising these polynucleotides, recombinant host cells, plants and insects transfected with the polynucleotides or with DNA derived therefrom, respectively, as well as to glycoproteins produced in these systems.

Glycoproteins exhibit a variety and complexity of carbohydrate units, the composition and arrangement of the carbohydrates being characteristic of different organisms. The oligosaccharide units of the glycoproteins have a number of tasks, e.g. they are important in regulating metabolism, they are involved in transmitting cell-cell interactions, they determine the circulation periods of proteins in circulation, and they are decisive for recognizing epitopes in antigen-antibody reactions.

The glycosylation of glycoproteins starts in the endoplasmatic reticulum (ER), where the oligosaccharides are either bound to asparagine side chains by N-glycosidic bonds or to serine or threonine side chains by O-glycosidic bonds. The N-bound oligo-saccharides contain a common core from a penta-saccharide unit which consists of three mannose and two N-acetyl glucose amine residues. To modify the carbohydrate units further, the proteins are transported from the ER to the Golgi complex. The structure of the N-bound oligosaccharide units of glycoproteins is determined by their conformation and by the composition of the glycosyl transferases of the Golgi compartments in which they are processed.

It has been shown that the core pentasaccharide unit of the N-glycans of some plants is substituted by β1,2-bound xylose and α1,3-bound fucose (Lerouge et al., 1998, Plant Mol. Biol. 38, 31–48; Rayon et al., 1998, J. Exp. Bot. 49, 1463–1472). The hepta-saccharide "$MMXF^3$" constitutes the main oligosaccharide type in plants (Kurosaka et al., 1991, J. Biol. Chem., 266, 4168–4172; Wilson and Altmann, 1998, Glycoconj. J. 15, 1055–1070). These structures are also termed complex N-glycans or mannose-deficient or truncated N-glycans, respectively. The α-mannosyl residues may be further replaced by GlcNAc, to which galactose and fucose are bound so that a structure is prepared which corresponds to the human Lewis a-epitope (Melo et al., 1997, FEBS Lett 415, 186–191; Fitchette-Laine et al., 1997, Plant J. 12, 1411–1417).

Neither β1,2-xylose nor the α1,3-bound fucose exist in mammalian glycoproteins. It has been found that the β1,2-xylose together with α1,3-fucose plays an important role in the epitope recognition of antibodies which are directed against plant N-bound oligosaccharides, and thereby trigger immune reactions in human or animal bodies against these oligosaccharides (Faye et al., 1993, Anal. Biochem. 209, 104–108). The β1,2-xylose and/or α1,3-fucose containing N-glycans furthermore seem to be one of the main causes for the wide-spread allergic cross reactivity between various plant and insect allergens and is also termed "cross-reactive carbohydrate determinant" (CCD). Due to the frequent occurrence of immunological cross reactions, the CCDs moreover mask allergy diagnoses.

The immunological reactions triggered in the human body by plant proteins are the main problem in the medicinal use of recombinant human proteins produced in plants. To circumvent this problem, β1,2-xylosylation together with α1,3-fucosylation would have to be prevented. According to a study, a mutant of the plant Arabidopsis thaliana was isolated in which the activity of N-acetyl-glucosaminyl transferase I, the first enzyme in the biosynthesis of complex glycans, is missing. The biosynthesis of the complex glycoproteins in this mutant thus is disturbed. Nevertheless, these mutant plants are capable of developing normally under certain conditions (A. Schaewen et al, 1993, Plant Physiol. 102; 1109–1118).

To block specifically the transfer of the β1,2-xylose to an oligosaccharide without also interfering in other glycosylation steps, solely that enzyme would have to be inactivated which is directly responsible for this specific glycosylation, i.e. the β1,2-xylosyltransferase. This transferase which only occurs in plants and some non-vertebrate animal species, e.g. in *Schistosoma* sp. (Khoo et al., 1997, Glycobiology 7, 663–677) and snail (e.g. Mulder et al., 1995, Eur. J. Biochem. 232, 272–283), yet not in human beings or in other vertebrates, would have to be in-activated on purpose or suppressed so that human proteins which are produced in plants or in plant cells, respectively, would no longer contain this immune-reaction-triggering epitope, as has been the case so far.

β1,2-xylosyltransferase transfers the D-xylose from UDP-xylose to the beta-linked mannose of plant N-linked oligosaccharides.

This enzyme was purified from soybean microsomes in 1997; Zeng et al.: J. Biol. Chem., 272, 31340–31347, 1997). According to this article, the best acceptor for xylose transfer was $GlcNAc_2Man_3GlcNAc_2$-T, but $GlcNAc_1Man_3GlcNAc_2$, with the GLcNAc on the 3-branch, was also a good acceptor. Furthermore, a number of other N-linked oligosaccharides were poor acceptors, especially those with galactose units at the nonreducing termini.

In the article by Rayon et al. (Plant Physiology, 1999, 119, 725–733) it is mentioned that Arabidopsis proteins are N-glycosylated by high-mannose-type N-glycans and by xylose- and fucose containing oligosaccharides. TEZUKA et al. (Eur. J. Biochem. 203, 401–413 (1992)) measured the activities of different enzymes, for example β1,2-xylosyltransferase in the Golgi fraction of suspension-cultured cells of sycamore. They demonstrated that xylose was transferred onto the inner mannose by β1,2-xylosyltransferase. Furthermore, they mentioned that xylose containing oligosaccharides are widely distributed throughout the plant kingdom although xylose containing N-linked oligosaccharides were also found in glycoproteins from gastropods and Chlorophyceae.

For the specific supression or inactivation of proteins it is best to carry this out at the level of transcription and translation step, respectively. For this it is necessary to isolate and sequence the nucleotide sequence which codes for the active protein.

As mentioned above, the soybean β1,2-xylosyltransferase was isolated and purified in 1997. Only a part of the xylosyltransferase cDNA has been isolated, s. WO99/29835 A1; SEQ ID NO 6 and 7), however, the complete cDNA, which codes for the active protein could not be isolated and characterized so far. The reason why the nucleotide sequence has not been identified so far could be major problems in the procedure due to very low abundance of the mRNA which codes for the xylosyltransferase in the organisms, as for example soybeans. Until now, although several groups have tried to identify the entire nucleotide sequence of this gene, usually from soybeans, it was not possible to produce full length cDNA which corresponds to the xylosyltransferase mRNA with the help of conventional methods known to be effective in usual cases, for example with the help of the RACE-amplification (rapid amplification of cDNA ends). With this method unknown sequences are amplified with the help of specific amplification primers. Potential reasons for unsuccessful 5'-RACE experiments can be an inadequate choice of specific PCR primers as well as the presence of reverse transcriptase-inhibiting components during cDNA synthesis.

One problem of the isolated soybean β1,2-xylosyl transferase is that its solubility and activity depends on the presence of detergents.

Additionally to the problem of the extremely low concentration of β1,2-xylosyltransferase mRNA there is furthermore the problem that the secondary structure at the 5'-end of the RNA seems to hinder the amplification of this region. In these cases, the RACE amplification which is in itself a sensitive method, does not result in the correct and complete xylosyltransferase-cDNA sequence.

It is of course also very likely that the mRNA and the cDNA derived thereof, beside the fact that it is present only in very low concentrations, recombines and mutates very easily in the course of the various manipulations. For these and other potential reasons the cloning and the expression of this specific gene was impossible until now.

It is an object of the present invention to clone and to sequence the whole gene which codes for a plant β1,2-xylosyltransferase, and to prepare vectors comprising this gene or an altered DNA or a DNA derived therefrom, to transfect plants as well as cells thereof with one of these vectors, to produce glycoproteins that do not contain the normally occurring β1,2-xylose, as well as to provide corresponding methods therefor.

A further object is the production of large quantities of purified recombinant enzyme in order to allow in vitro synthesis of homogenous N-glycans or glycoconjugates containing β1,2-xylose. This will aid the further elucidation of the role of β1,2-xylose in the immunogenicity and allergenicity of plant glycoproteins.

The object according to the invention is achieved by a DNA mole cule comprising a sequence according to SEQ ID NO: 8 with an open reading frame from base pair 227 to base pair 1831 or being at least 50% homologous to the above sequence or hybridizing with the above-indicated sequence under stringent conditions, or comprising a sequence which has degenerated to the above DNA sequence due to the genetic code, the sequence coding for a plant protein which has β1,2-xylosyltransferase activity or is complementary thereto. This complete sequence which has never been described is particularly useful for experiments, analysis and production processes which concern the β1,2-xylosyltransferase activity. This sequence can be used especially for the inactivation or suppression of the β1,2-xylosyltransferase as well as for overexpression and production of the recombinant enzyme.

Upon searching GenBank+EMBL+DDBJ+PDB databases using the soybean xylosyltransferase-derived peptides as mentioned above several polypeptide sequences (from *Arabidopsis* and *Drosophila*) with significant homologies were retrieved. However, these sequences were otherwise unrelated to each other as well as to the β1,2-xylosyltransferase sequence finally identified. Successful retrieval of candidate sequence for β1,2-xylosyltransferase was possible only by properly assembling three soybean β1,2-xylosyl transferase-derived peptide sequences to a single sequence. All search strategies we used according to the present state of the art (i.e. using the peptide sequences separately or in combination with each other) did not lead to a successful retrieval of the correct sequence for β1,2-xylosyltransferase.

The isolation and purification of this gene was achieved by searching in the DDBJ+GenBank+EMBL+PDB-databases corresponding sequences to three known peptides (used as assembled peptides) of the soybean xylosyltransferase (Patent WO99/29835 A1, SEQ ID NO: 3 and 5). It was found that one DNA sequence of *Arabidopsis thaliana* which has not yet been assigned to any protein before showed homology to two of the three peptides. With the help of the gene-finder program a predicted protein sequence was found according to which sequence specific primers for a RT-PCR were designed. It was possible to produce a first strand cDNA corresponding to the mRNA of the *A. thaliana*-xylosyltransferase gene after which the first strand cDNA was subjected to a PCR using the specifically designed primers. The reason for the successful production of *A. thaliana* xylosyltransferase-cDNA may be on the one hand that the xylosyltransferase-mRNA of *A. thaliana* is less problematic compared to other plant species, on the other hand the PCR was performed with optimally designed gene-specific primers.

The open reading frame of the SEQ ID NO: 8 codes for a protein with 534 amino acids and with a theoretical molecular weight of 60.2 kDa, a transmembrane portion presumably being present in the region between I1e11 and Phe29. The calculated pI value of the encoded protein of the sequence according to SEQ ID NO: 9 is 7.52.

The activity of the plant β1,2-xylosyltransferase is detected by a method and measured, the xylosyltransferase being added to a sample containing UDP-xylose and a labelled acceptor (e.g. a glycopeptide or labelled oligosaccharide). After the reaction time, the content of bound xylose is measured. The activity of the xylosyltransferase in this case is seen as positive if the activity measurement is higher by at least 10 to 20%, in particular at least 30 to 50%, than the activity measurement of the negative control. The structure of the oligosaccharide may additionally be verified by means of HPLC. Such protocols are prior art (Staudacher et al., 1998, Anal. Biochem. 246, 96–101; Staudacher et al., 1991, Eur. J. Biochem. 199, 745–751). Whether the xylose is bound or not to the acceptor substrate can furthermore be determined by measuring the mass of the product by means of mass spectrometry.

The pairing of two DNA molecules can be changed by selection of the temperature and ionic strength of the sample. By stringent conditions, according to the invention conditions are understood which allow for an exact, stringent, binding. For instance, the DNA molecules are hybridized in 7% sodium dodecyl sulfate (SDS), 0.5M $NaPO_4$, pH 7.0, 1 mM EDTA at 50° C., and washed with 1% SDS at 42° C.

Whether sequences have an at least 50% homology to SEQ ID NO: 8 can be determined e.g. by means of the program FastDB of EMBL or SWISSPROT data bank.

There exist a number of relevant differences between recombinant β1,2-xylosyltransferase encoded by the DNA molecule of the present invention and the respective enzyme from soybean as described in WO99/29835 A1:

1. The recombinant enzyme is soluble without detergents (e.g. Triton X-100), whereas the solubility of the enzyme from soybean depends on the presence of detergents.
2. The recombinant enzyme is fully active in the absence of detergents (e.g. Triton X-100).
3. The recombinant enzyme is N-glycosylated, whereas the enzyme from soybean is described to be unglycosylated.
4. The enzyme from *A. thaliana* exhibits full enzymatic activity also as a truncated form lacking the 32 N-terminal amino acids.
5. In contrast to the enzyme from soybean the enzyme from *A. thaliana* has a broad pH-optimum and shows pronounced activity in the range of pH 6–8.

6. The cDNA sequence coding for the soybean enzyme corresponds only to amino acids (aa) 199–469 of the *A. thaliana* protein, see FIG. 11.
7. The cDNA sequence coding for *A. thaliana* xylosyltransferase contains two insertions (corresponding to aa 375–382 and aa 425–429 of the predicted protein sequence) compared to the partial sequence of the soybean enzyme, see FIG. 11.
8. None of the five peptides (see FIG. 4 of WO99/29835 A1) isolated from the soybean enzyme is identical to the corresponding regions of the enzyme from *A. thaliana:*

Peptide SEQ ID NO. 1: homologous to aa 411–422 of the *A. thaliana* enzyme

Peptide SEQ ID NO. 2: homologous to aa 192–205 of the *A. thaliana* enzyme

Peptide SEQ ID NO. 3: homologous to aa 451–477 of the *A. thaliana* enzyme

Peptide SEQ ID NO. 4: homologous to aa 191–205 of the *A. thaliana* enzyme

Peptide SEQ ID NO. 5: homologous to aa 503–512 of the *A. thaliana* enzyme (remark: the cDNA sequence listed in WO99/29835 A1 does not contain a coding sequence for peptide 5).

Therefore the DNA molecule according to the present invention is particularly advantageous since it encodes for an active recombinant enzyme which shows surprisingly advantageous characteristics and effects over the known purified enzyme.

Preferably, the sequence of the DNA molecule of the invention encodes a protein with a β1,2-xylosyltransferase activity. This specific protein is especially useful for analysis, experiments and production methods which relate to the β1,2-xylosyltransferase.

Preferably, the DNA molecule according to the invention is at least 70%, preferably at least 80%, particularly preferred at least 95%, homologous with the sequence according to SEQ ID NO: 8. This sequence codes for a particularly active β1,2-xylosyltransferase. The homology preferably is determined with a program which recognizes insertions and deletions and which does not consider these in the homology calculation.

According to a further advantageous embodiment, the DNA molecule comprises 1750 to 1850, in particular 1831, base pairs.

In doing so, it is particularly advantageous if one of the above-indicated DNA molecules is covalently associated with a detectable marker substance. As the marker (labelling) substance, any common marker can be used, such as, e.g., fluorescent, luminescent, radioactive markers, biotin, etc. In this manner, reagents are provided which are suitable for the detection, selection and quantitation of corresponding DNA molecules in solid tissue samples (e.g. from plants) or also in liquid samples, by means of hybridizing methods.

Preferably, the DNA molecule according to the invention includes a sequence which comprises a deletion, insertion and/or substitution mutation. The number of mutant nucleotides is variable and varies from a single one to several deleted, inserted or substituted nucleotides. It is also possible that the reading frame is shifted by the mutation. In such a "knock-out gene" it is merely important that the expression of a β1,2-xylosyltransferase is disturbed, and the formation of an active, functional enzyme is prevented. In doing so, the site of the mutation is variable, as long as expression of an enzymatically active protein is prevented. Preferably, the mutation in the catalytic region of the enzyme which is located in the C-terminal region. The method of inserting mutations in DNA sequences are well known to the skilled artisan, and therefore the various possibilities of mutageneses need not be discussed here in detail. Coincidental mutageneses as well as, in particular, directed mutageneses, e.g. the site-directed mutagenesis, oligonucleotide-controlled mutagenesis or mutageneses by aid of restriction enzymes may be employed in this instance.

The invention further provides a DNA molecule which codes for a ribozyme which comprises two sequence sections, each of which has a length of at least 10 to 15 base pairs each, which are complementary to sequence sections of an inventive DNA molecule as described above so that the ribozyme complexes and cleaves the mRNA which is transcribed by a natural β1,2-xylosyltransferase DNA molecule. The publication by John M. Burke "Clearing the way for ribozymes" (Nature Biotechnology 15:414–415; 1997) relates to the general mode of function of ribozymes. The ribozyme will recognize the mRNA of the β1,2-xylosyltransferase by complementary base pairing with the mRNA. Subsequently, the ribozyme will cleave and destroy the RNA in a sequence-specific manner, before the enzyme is translated. After dissociation from the cleaved substrate, the ribozyme will repeatedly hybridize with RNA molecules and act as specific endonuclease. In general, ribozymes may specifically be produced for inactivation of a certain mRNA, even if not the entire DNA sequence which codes for the protein is known. Ribozymes are particularly efficient if the ribosomes move slowly along the mRNA. In that case it is easier for the ribozyme to find a ribosome-free site on the mRNA. For this reason, slow ribosome mutants are also suitable as a system for ribozymes (J. Burke, 1997, Nature Biotechnology; 15, 414–415).

One possible way is also to use a varied form of a ribozmye, i.e. a minizyme. Minizymes are efficient particularly for cleaving larger mRNA molecules. A minizyme is a hammer head ribozyme which has a short oligonucleotide linker instead of the stem/loop II. Dimer-minizymes are particularly efficient (Kuwabara et al., 1998, Nature Biotechnology, 16; 961–965).

A further aspect of the invention relates to a biologically functional vector which comprises one of the above-indicated DNA molecules. For transfection into host cells, an independent vector capable of amplification is necessary, wherein, depending on the host cell, transfection mechanism, task and size of the DNA molecule, a suitable vector can be used. Since a large number of different vectors is known, an enumeration thereof would go beyond the limits of the present application and there fore is done without here, particularly since the vectors are very well known to the skilled artisan (as regards the vectors as well as all the techniques and terms used in this specification which are known to the skilled artisan, cf. also Maniatis). Ideally, the vector has a small molecule mass and should comprise selectable genes so as to lead to an easily recognizable phenotype in a cell so thus enable an easy selection of vector-containing and vector-free host cells. To obtain a high yield of DNA and corresponding gene products, the vector should comprise a strong promoter, as well as an enhancer, gene amplification signals and regulator sequences. For an autonomous replication of the vector, furthermore, a replication origin is important. Polyadenylation sites are responsible for correct processing of the mRNA and splice signals for the RNA transcripts. If phages, viruses or virus particles are used as the vectors, packaging signals will control the packaging of the vector DNA. For instance, for transcription in plants, Ti plasmids are suitable, and for transcription in insect cells, baculoviruses, and in insects, respectively, transposons, such as the P element.

If the above-described inventive vector is inserted into a plant or into a plant cell, a post-transcriptional suppression of the gene expression of the endogenous β1,2-xylosyltransferase gene is attained by transcription of a transgene homologous thereto or of parts thereof, in sense orientation. For this sense technique, furthermore, reference is made to the publications by Baucombe 1996, Plant. Mol. Biol., 9:373–382, and Brigneti et al., 1998, EMBO J. 17:6739–6746. This strategy of "gene silencing" is an effective way of suppressing the expression of the β1,2-xylosyltransferase gene, cf. also Waterhouse et al., 1998, Proc. Natl. Acad. Sci. USA, 95:13959–13964.

Furthermore, the invention relates to a biologically functional vector comprising a DNA molecule according to one of the above-described embodiments, being inversely orientated with respect to the promoter. If this vector is transfected in a host cell, an "antisense mRNA" will be read which is complementary to the mRNA of the β1,2-xylosyltransferase and complexes the latter. This bond will either hinder correct processing, transportation, stability or, by preventing ribosome annealing, it will hinder translation and thus the normal gene expression of the β1,2-xylosyltransferase.

Although the entire sequence of the DNA molecule could be inserted into the vector, partial sequences thereof because of their smaller size may be advantageous for certain purposes. With the antisense aspect, e.g., it is important that the DNA molecule is large enough to form a sufficiently large antisense mRNA which will bind to the transferase mRNA. A suitable antisense RNA molecule comprises, e.g., from 50 to 200 nucleotides since many of the known, naturally occurring antisense RNA molecules comprise approximately 100 nucleotides.

For a particularly effective inhibition of the expression of an active β1,2-xylosyltransferase, a combination of the sense technique and the antisense technique is suitable (Waterhouse et al., 1998, Proc. Natl. Acad. Sci., USA, 95:13959–13964).

Advantageously, rapidly hybridizing RNA molecules are used. The efficiency of antisense RNA molecules which have a size of more than 50 nucleotides will depend on the annealing kinetics in vitro. Thus, e.g., rapidly annealing antisense RNA molecules exhibit a greater inhibition of protein expression than slowly hybridizing RNA molecules (Wagner et al., 1994, Annu. Rev. Microbiol., 48:713–742; Rittner et al., 1993, Nucl. Acids Res., 21: 1381–1387). Such rapidly hybridizing antisense RNA molecules particularly comprise a large number of external bases (free ends and connecting sequences), a large number of structural subdomains (components) as well as a low degree of loops (Patzel et al. 1998; Nature Biotechnology, 16; 64–68). The hypothetical secondary structures of the antisense RNA molecule may, e.g., be determined by aid of a computer program, according to which a suitable antisense RNA DNA sequence is chosen.

Different sequence regions of the DNA molecule may be inserted into the vector. One possibility consists, e.g., in inserting into the vector only that part which is responsible for ribosome annealing. Blocking in this region of the mRNA will suffice to stop the entire translation. A particularly high efficiency of the antisense molecules also results for the 5'- and 3'-non translated regions of the gene.

The invention also relates to a biologically functional vector which comprises one of the two last-mentioned DNA molecules (mutation or ribozyme-DNA molecule). What has been said above regarding vectors also applies in this instance.

According to the invention, there is provided a method of preparing a cDNA comprising the DNA molecule of the invention, where in RNA is isolated from a plant cell, in particular from leaf cells, by means of which a reverse transcription is carried out after the addition of a reverse transcriptase and primers. The individual steps of this method are carried out according to protocols known per se. For the reverse transcription, on the one hand, it is possible to produce the cDNA of the entire mRNA with the help of oligo(dT) primers, and only then to carry out a PCR by means of selected primers so as to prepare DNA molecules comprising the β1,2-xylosyltransferase gene. On the other hand, the selected primers may directly be used for the reverse transcription so as to obtain short, specific cDNA. The suitable primers may be prepared e.g. synthetically according to the pattern of cDNA sequences of the transferase.

The invention furthermore relates to a method of cloning a β1,2-xylosyltransferase, characterized in that the DNA molecule of the invention is cloned into a vector which subsequently is transfected into a host cell or host, respectively, wherein, by selection and amplification of transfected host cells, cell lines are obtained which express the active β1,2-xylosyltransferase. The DNA molecule is inserted into the vector by aid of restriction endo-nucleases, e.g. For the vector, there applies what has already been said above. What is important in this method is that an efficient host-vector system is chosen. To obtain an active enzyme, eukaryotic host cells are particularly suitable. One possible way is to transfect the vector in insect cells. In doing so, in particular an insect virus would have to be used as vector, such as, e.g., baculovirus.

Of course, plants or plant cells, human or other vertebrate cells can also be transfected, in which case the latter would express an enzyme foreign to them.

Preferably, a method of preparing recombinant host cells, in particular plant cells or plants, respectively, with a suppressed or completely stopped β1,2-xylosyltransferase production is provided, which is characterized in that at least one of the vectors according to the invention, i.e. that one comprising the inventive DNA molecule, the mutant DNA molecule or the DNA molecule coding for ribozymes or the one comprising the DNA molecule in inverse orientation to the promoter, is inserted into the host cell or plant, respectively. What has been said above for the transfection also is applicable in this case.

As the host cells, plant cells may, e.g., be used, wherein, e.g., the Ti plasmid with the *agrobacterium* system is eligible. With the *agrobacterium* system it is possible to transfect a plant directly: agrobacteria cause root stem galls in plants. If agrobacteria infect an injured plant, the bacteria themselves do not get into the plant, but they insert the recombinant DNA portion, the so-called T-DNA, from the annular, extrachromosomal, tumour-inducing Ti-plasmid into the plant cells. The T-DNA, and thus also the DNA molecule inserted therein, are installed in the chromosomal DNA of the cell in a stable manner so that the genes of the T-DNA will be expressed in the plant.

There exist numerous known, efficient transfection mechanisms for different host systems. Some examples are electroporation, the calcium phosphate method, microinjection, liposome method.

Subsequently, the transfected cells are selected, e.g. on the basis of antibiotic resistences for which the vector comprises genes, or other marker genes. Then the transfected cell lines are amplified, either in small amounts, e.g. in Petri dishes, or in large amounts, e.g. in fermentors. Furthermore, plants have a particular characteristic, i.e. they are capable to re-develop from one (transfected) cell or from a protoplast, respectively, to a complete plant which can be grown.

Depending on the vector used, processes will occur in the host so that the enzyme expression will be suppressed or completely blocked:

If the vector comprising the DNA molecule with the deletion, insertion or substitution mutation is transfected, a homologous recombination will occur: the mutant DNA molecule will recognize the identical sequence in the genome of the host cell despite its mutation and will be inserted exactly on that place so that a "knock-out gene" is formed. In this manner, a mutation is introduced into the gene for the β1,2-xylosyltransferase which is capable of inhibiting the faultless expression of the β1,2-xylosyltransferase. As has been explained above, with this technique it is important that the mutation suffices to block the expression of the active protein. After selection and amplification, the gene may be sequenced as an additional check so as to determine the success of the homologous recombination or the degree of mutation, respectively.

If the vector comprising the DNA molecule coding for a ribozyme is transfected, the active ribozyme will be expressed in the host cell. The ribozyme complexes the complementary mRNA sequence of the β1,2-xylosyltransferase at least at a certain site, cleaves this site, and in this manner it can inhibit the translation of the enzyme. In this host cell as well as in cell lines, or optionally, plant, respectively, derived therefrom, β1,2-xylosyltransferase will not be expressed.

In case the vector comprises the inventive DNA molecule in sense or inverse direction to the promoter, a sense or antisense-mRNA will be expressed in the transfected cell (or plant, respectively). The antisense mRNA is complementary at least to a part of the mRNA sequence of the β1,2-xylosyltransferase and may likewise inhibit translation of the enzyme. As an example of a method of suppressing the expression of a gene by antisense technique, reference is made to the publication by Smith et al., 1990, Mol. Gen. Genet. 224:477–481, wherein in this publication the expression of a gene involved in the maturing process of tomatoes is inhibited. Double-stranded RNA (dsRNA) has recently been shown to trigger sequence-specific gene silencing in a wide variety of organisms, including nematodes, plants, trypanosomes, fruit flies and planaria; an as yet uncharacterized RNA trigger has been shown to induce DNA methylation in several different plant systems leading to selective interference with gene function (for review see Fire A., 1999, Trends Genet 15 (9): 358–363).

In all the systems, expression of the β1,2-xylosyltransferase is at least suppressed, preferably even completely blocked. The degree of the disturbance of the gene expression will depend on the degree of complexing, homologous recombination, on possible subsequent coincidental mutations and on other processes in the region of the genome. The transfected cells are checked for β1,2-xylosyltransferase activity and selected.

Moreover, it is possible to still further increase the above-described suppression of the expression of the β1,2-xylosyltransferase by introducing into the host a vector comprising a gene coding for a mammalian protein, e.g. β1,4-galactosyltransferase, in addition to the insertion of an above-described vector. Xylosylation may be reduced by the action of other mammalian enzymes, the combination of the inhibition of the expression of an active β1,2-xylosyltransferase by means of the inventive vector and by means of a mammalian enzyme vector being particularly efficient.

Any type of plant may be used for transfection, e.g. mung bean, tobacco plant, tomato and/or potato plant.

Another advantageous method of producing recombinant host cells, in particular plant cells, or plants, respectively, consists in that the DNA molecule comprising the mutation is inserted into the genome of the host cell, or plant, respectively, in the place of the non-mutated homologous sequence (Schaefer et al., 1997, Plant J.; 11(6):1195–1206). This method thus does not function with a vector, but with a pure DNA molecule. The DNA molecule is inserted into the host e.g. by gene bombardment, microinjection or electroporation, to mention just three examples. As has already been explained, the DNA molecule binds to the homologous sequence in the genome of the host so that a homologous recombination and thus reception of the deletion, insertion or substitution mutation, respectively, will result in the genome: Expression of the β1,2-xylosyltransferase can be suppressed or completely blocked, respectively.

Preferably, recombinant plants or plant cells, respectively, are provided which have been prepared by one of the methods described above, their β1,2-xylosyltransferase production being suppressed or completely blocked, respectively. Preferably, their β1,2-xylosyltransferase activity is less than 50%, in particular less than 20%, particularly preferred 0%, of the β1,2-xylosyltransferase activity occurring in natural plants or plant cells, respectively. The advantage of these plants or plant cells, respectively, is that the glycoproteins produced by them do not comprise any or hardly comprise any β1,2-bound xylose. If products of these plants are taken up by human or vertebrate bodies, there will be no immune reaction due to the β1,2-xylose epitope.

The invention also relates to a PNA molecule comprising a base sequence complementary to the sequence of the DNA molecule according to the invention. PNA (peptide nucleic acid) is a DNA-like sequence, the nucleobases being bound to a pseudo-peptide backbone. PNA generally hybridizes with complementary DNA-, RNA- or PNA-oligomers by Watson-Crick base pairing and helix formation. The peptide backbone ensures a greater resistance to enzymatic degradation. The PNA molecule thus is an improved antisense agent.

Neither nucleases nor proteases are capable of attacking a PNA molecule. The stability of the PNA molecule, if bound to a complementary sequence, comprises a sufficient steric blocking of DNA and RNA polymerases, reverse transcriptase, telomerase and ribosomes. The publication by Pooga et al., "Cell penetrating PNA constructs regulate galanin receptor levels and modify pain transmission in vivo" (Nature Biotechnology 16:857–861; 1998) relates to PNA molecules in general and specifically to a PNA molecule that is complementary to human galanin receptor type 1 mRNA.

If the PNA molecule comprises the above-mentioned sequence, it will bind to the DNA or to a site of the DNA, respectively, which codes for β1,2-xylosyltransferase and in this way is capable of inhibiting transcription of this enzyme. As it is neither transcribed nor translated, the PNA molecule will be prepared synthetically, e.g. by aid of the the t-Boc technique.

Advantageously, a PNA molecule is provided which comprises a base sequence which corresponds to the sequence of the inventive DNA molecule. This PNA molecule will complex the mRNA or a site of the mRNA of β1,2-xylosyltransferase so that the translation of the enzyme will be inhibited. Similar arguments as set forth for the antisense RNA apply in this case. Thus, e.g., a particularly efficient complexing region is the translation start region or also the 5'-non-translated regions of mRNA.

A further aspect of the present invention relates to a method of preparing plants or plant cells, respectively, in particular plant cells which comprise a blocked expression of the β1,2-xylosyltransferase at the transcription or translation level, respectively, which is characterized in that inventive PNA molecules are inserted in the cells. To insert the PNA molecule or the PNA molecules, respectively, in the cell, again conventional methods, such as, e.g., electroporation or microinjection, are used. Particularly efficient is insertion if the PNA oligomers are bound to cell penetration peptides, e.g. transportan or pAntp (Pooga et al., 1998, Nature Biotechnology, 16; 857–861).

The invention provides a method of preparing recombinant glycoproteins which is characterized in that the inventive, recombinant plants or plant cells, respectively, whose β1,2-xylosyltransferase production is suppressed or completely blocked, respectively, or plants or cells, respectively, in which the PNA molecules have been inserted according to the method of the invention, are transfected with the gene that expresses the glycoprotein so that the recombinant glycoproteins are expressed. In doing so, as has already been described above, vectors comprising genes for the desired proteins are transfected into the host or host cells, respectively, as has also already been described above. The transfected plant cells will express the desired proteins, and they have no or hardly any β1,2-bound xylose. Thus, they do not trigger the immune reactions already mentioned above in the human or vertebrate body. Any proteins may be produced in these systems.

Advantageously, a method of preparing recombinant human glycoproteins is provided which is characterized in that the recombinant plants or plant cells, respectively, whose β1,2-xylosyltransferase production is suppressed or completely blocked, or plants or cells, respectively, in which PNA molecules have been inserted according to the method of the invention, are transfected with the gene that expresses the glycoprotein so that the recombinant glycoproteins are expressed. By this method it becomes possible to produce human proteins in plants (plant cells) which, if taken up by the human body, do not trigger any immune reaction directed against β1,2-bound xylose residues. There, it is possible to utilize plant types for producing the recombinant glycoproteins which serve as food stuffs, e.g. banana, potato and/or tomato. The tissues of this plant comprise the recombinant glycoprotein so that, e.g. by extraction of the recombinant glycoprotein from the tissue and subsequent administration, or directly by eating the plant tissue, respectively, the recombinant glycoprotein is taken up in the human body.

Preferably, a method of preparing recombinant human glycoproteins for medical use is provided, wherein the inventive, recombinant plants or plant cells, respectively, whose β1,2-xylosyltransferase production is suppressed or completely blocked, respectively, or plants or cells, respectively, into which the PNA molecules have been inserted according to the method of the invention, are transfected with the gene that expresses the glycoprotein so that the recombinant glycoproteins are expressed. In doing so, any protein can be used which is of medical interest.

Moreover, the present invention relates to recombinant glycoproteins according to a method described above, wherein they have been prepared in plant systems and wherein their peptide sequence comprises less than 50%, in particular less than 20%, particularly preferred 0%, of the β1,2-bound xylose residues occurring in proteins expressed in non-xylosyltransferase-reduced plant systems. Naturally, glycoproteins which do not comprise β1,2-bound xylose residues are to be preferred. The amount of β1,2-bound xylose will depend on the degree of the above-described suppression of the β1,2-xylosyltransferase.

Preferably, the invention relates to recombinant human glycoproteins which have been produced in plant systems according to a method described above and whose peptide sequence comprises less than 50%, in particular less than 20%, particularly preferred 0%, of the β1,2-bound xylose residues occurring in the proteins expressed in non-xylosyltransferase-reduced plant systems.

A particularly preferred embodiment relates to recombinant human glycoproteins for medical use which have been prepared in plant systems according to a method described above and whose peptide sequence comprises less than 50%, in particular less than 20%, particularly preferred 0%, of the β1,2-bound xylose residues occurring in the proteins expressed in non-xylosyltransferase-reduced plant systems.

The glycoproteins according to the invention may include other bound oligosaccharide units specific for plants, whereby—in the case of human glycoproteins—they differ from these natural glycoproteins. Nevertheless, by the glycoproteins according to the invention, a slighter immune reaction or no immune reaction at all, respectively, is triggered in the human body, since, as has already been explained in the introductory portion of the specification, the β1,2-bound xylose residues, together with α1,3-fucose residues, are the main cause for the immune reactions or cross immune reaction, respectively, to plant glycoproteins.

A further aspect comprises a pharmaceutical composition comprising the glycoproteins according to the invention. In addition to the glycoproteins of the invention, the pharmaceutical composition comprises further additions common for such compositions. These are, e.g., suitable diluting agents of various buffer contents (e.g. Tris-HCl, acetate, phosphate, pH and ionic strength), additives, such as tensides and solubilizers (e.g. Tween 80, Polysorbate 80), preservatives (e.g. Thimerosal, benzyl alcohol), adjuvants, antioxidants (e.g. ascorbic acid, sodium metabisulfite), emulsifiers, fillers (e.g. lactose, mannitol), covalent bonds of polymers, such as polyethylene glycol, to the protein, incorporation of the material in particulate compositions of polymeric compounds, such as polylactic acid, polyglycolic acid, etc. or in liposomes, auxiliary agents and/or carrier substances which are suitable in the respective treatment. Such compositions will influence the physical condition, stability, rate of in vivo liberation and rate of in vivo excretion of the glycoproteins of the invention.

The invention also provides a method of selecting DNA molecules which code for a β1,2-xylosyltransferase, in a sample, wherein the labelled DNA molecules of the invention or partial sequences thereof, are added to the sample, which bind to the DNA molecules that code for a β1,2-xylosyltransferase. The hybridized DNA molecules can be detected, quantitated and selected. For the sample to contain single strand DNA with which the labelled DNA molecules can hybridize, the sample is denatured, e.g. by heating.

One possible way is to separate the DNA to be assayed, possibly after the addition of endonucleases, by gel electrophoresis on an agarose gel. After having been transferred to a membrane of nitrocellulose, the labelled DNA molecules according to the invention are admixed which hybridize to the corresponding homologous DNA molecule ("Southern blotting").

Another possible way consists in finding homologous genes from other species by PCR-dependent methods using specific and/or de-generated primers, derived from the sequence of the DNA molecule according to the invention.

Advantageously the labelled DNA molecules of the invention or partial sequences thereof are immobilized onto carrier matrices. The use of DNA microarrays ("gene chips") is a further possible way to find homologous genes or to study the expression level of homologous genes. To this end, DNA representing either the entire genomic gene sequence, the full-length cDNA sequence, parts of these sequences or any combination of partial sequences, is immobilized onto carrier matrices, in order that homologous genes, after adding the sample to the carrier matrices, hybridize with the labelled DNA molecules (for examples see e.g. Ferea T. L. & Brown, P. O., 1999, Current Opinion in Genetics & Development 9: 715–722 and references cited herein).

Preferably, the sample for the above-identified inventive method comprises genomic DNA of a plant organism. By this method, a large number of plants or other species is assayed in a very rapid and efficient manner for the presence of the β1,2-xylosyltransferase gene. In this manner, it is respectively possible to select plants or individuals of other species which do not comprise this gene, or to suppress or completely block, respectively, the expression of the β1,2-xylosyltransferase in such plants or other organisms which comprise this gene, by an above-described method of the invention, so that subsequently they may be used for the transfection and production of (human) glycoproteins.

The invention also relates to DNA molecules which code for a β1,2-xylosyltransferase which have been selected according to the three last-mentioned methods and subsequently have been isolated from the sample. These molecules can be used for further assays. They can be sequenced and in turn can be used as DNA probes for finding β1,2-xylosyltransferases. These—labelled—DNA molecules will function for organisms, which are related to the organisms from which they have been isolated, more efficiently as probes than the DNA molecules of the invention.

A further aspect of the invention relates to a preparation of β1,2-xylosyltransferase cloned according to the invention which comprises isoforms having pI values of between 6.0 and 9.0, in particular between 7.50 and 8.00. The pI values of a protein is that pH value at which its net charge is zero and is dependent on the amino acid sequence, the glycosylation pattern as well as on the spatial structure of the protein. The β1,2-xylosyltransferase may comprise several isoforms which have a pI value in this range. The reason for the various isoforms of the transferase are, e.g., different glycosylations as well as limited proteolysis. The pI value of a protein can be determined by isoelectric focussing, which is known to the skilled artisan.

The main isoform of the enzyme has an apparent molecular weight of 60.2 kDa.

In particular, the preparation of the invention comprises an isoform having a pI value of 7.52.

The invention also relates to a method of preparing "plantified" carbohydrate units of human and other vertebrate glycoproteins or other glycoconjugates, wherein UDP-xylose as well as β1,2-xylosyltransferase encoded by an above-described DNA molecule are added to a sample that comprises a carbohydrate unit or a glycoprotein, respectively, so that xylose in β1,2-position is bound by the β1,2-xylosyltransferase to the carbohydrate unit or to the glycoprotein, respectively. By the method according to the invention for cloning β1,2-xylosyltransferase it is possible to produce large amounts of purified enzyme. To obtain a fully active transferase, suitable reaction conditions are provided.

The invention will be explained in more detail by way of the following examples and drawing figures to which, of course, it shall not be restricted. In detail, in the drawings, FIG. 1 shows the amino acid sequence of soybean peptide 2 and 3 (patent WO99/29835; SEQ ID NO: 3 and 5), the homology between these peptides and a *A. thaliana* sequence as well as the DNA sequence of four primers 1–4;

FIG. 2 shows the cDNA sequence of β1,2-xylosyltransferase including 226 nt of the 5'-untranslated region;

FIG. 3 shows the amino acid sequence of β1,2-xylosyltransferase derived therefrom;

Figure 6:
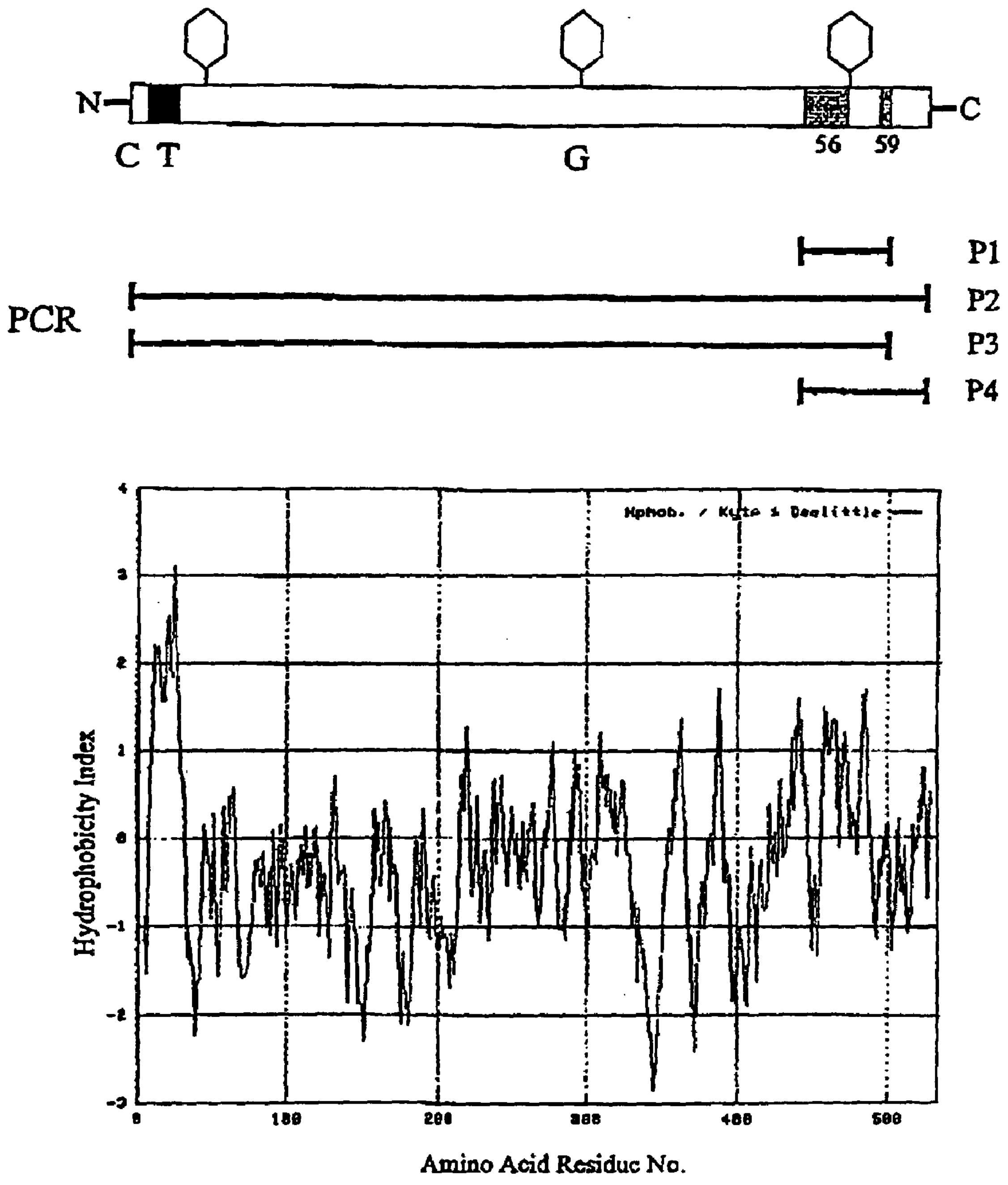
Figure 7:
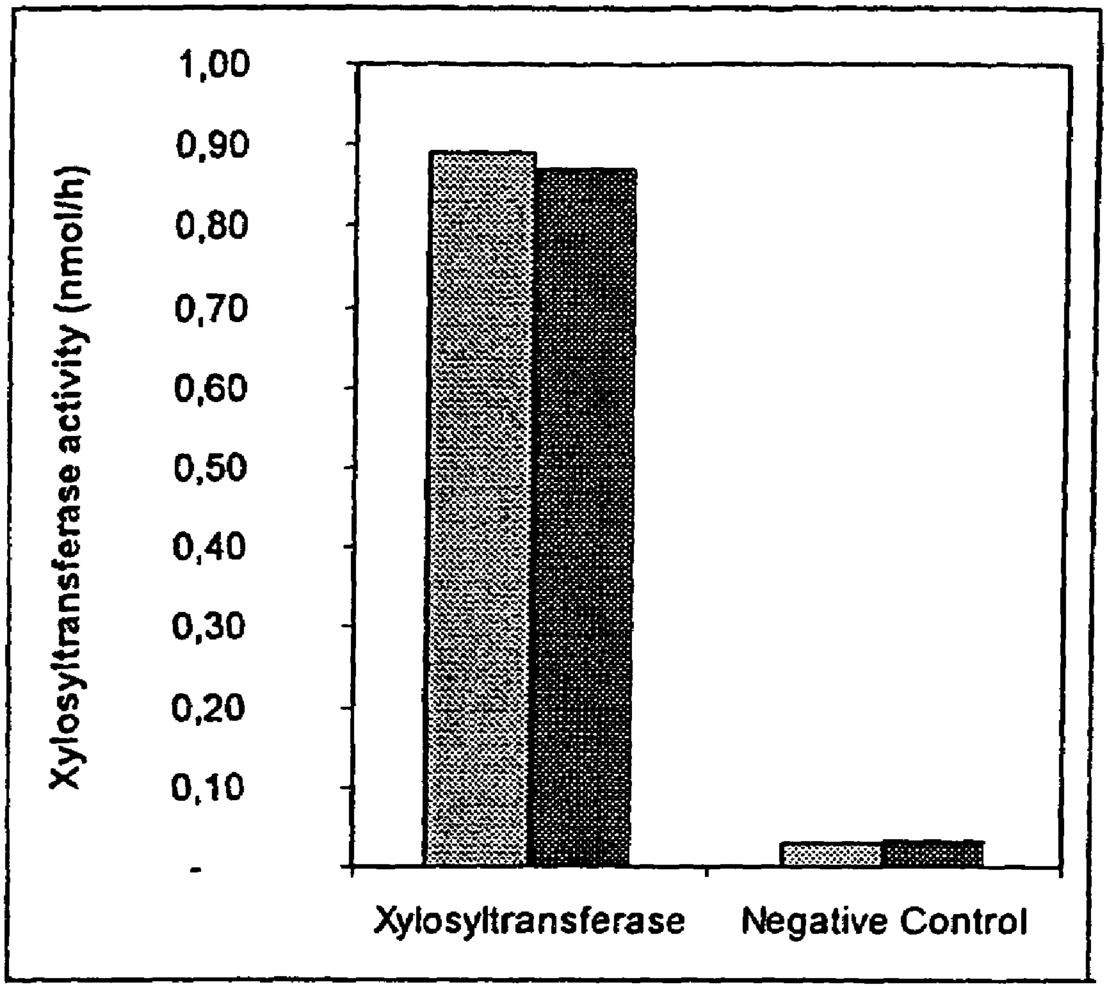
Figure 8A:
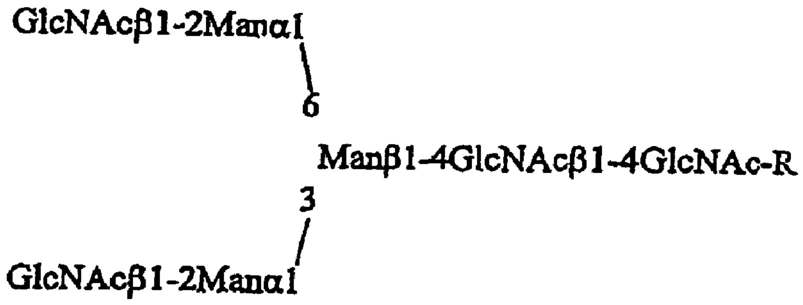
Figure 8B:
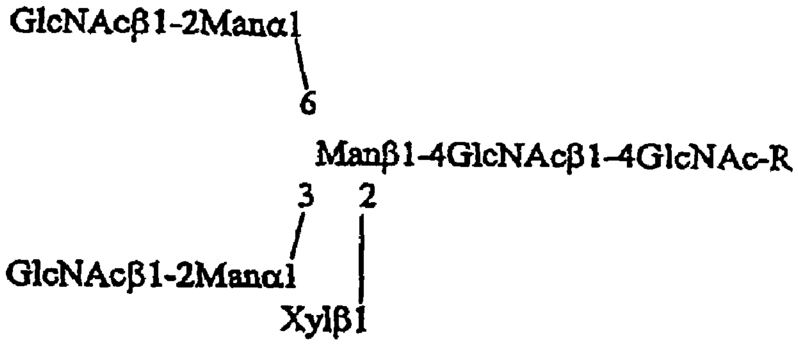
Figure 9:
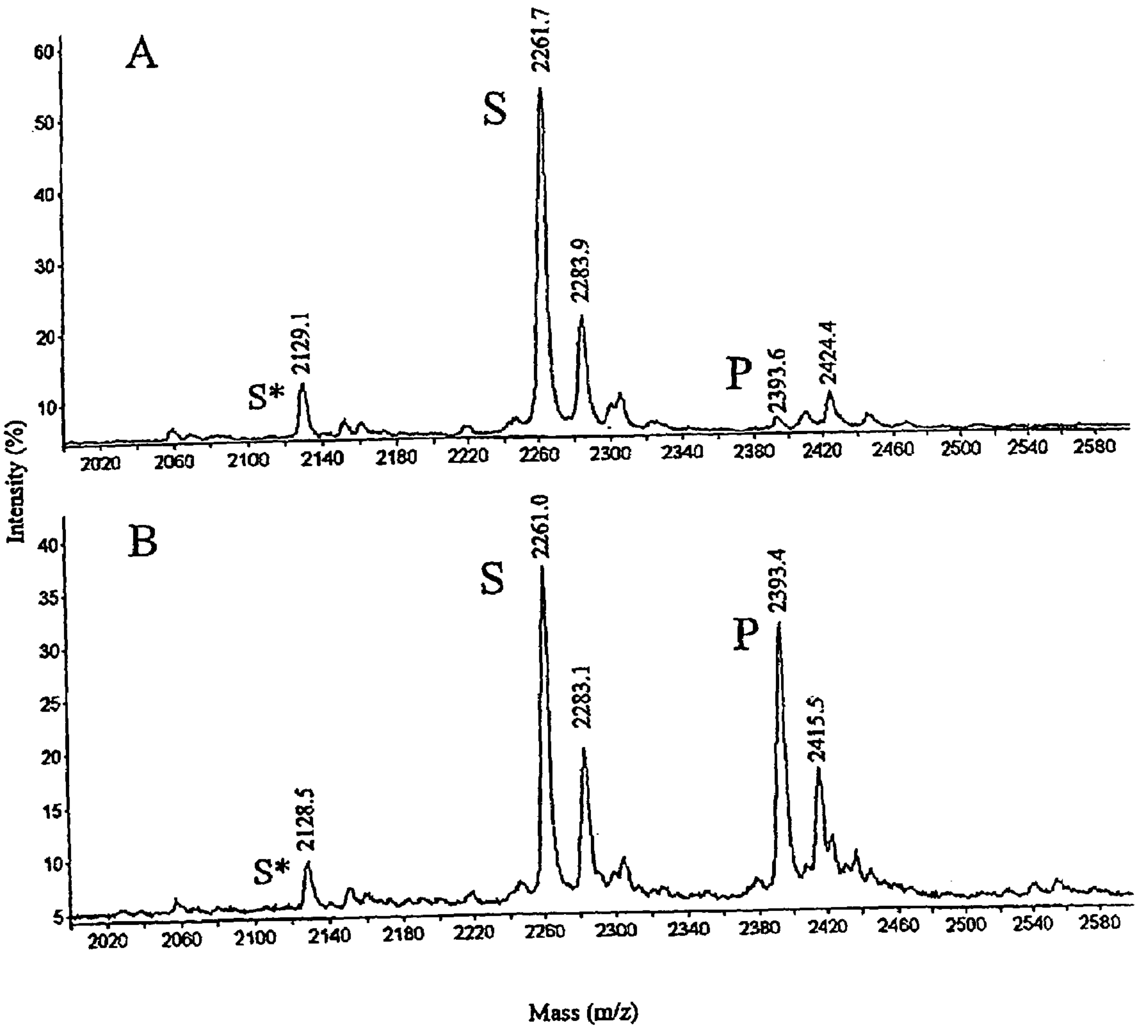
Figure 10:
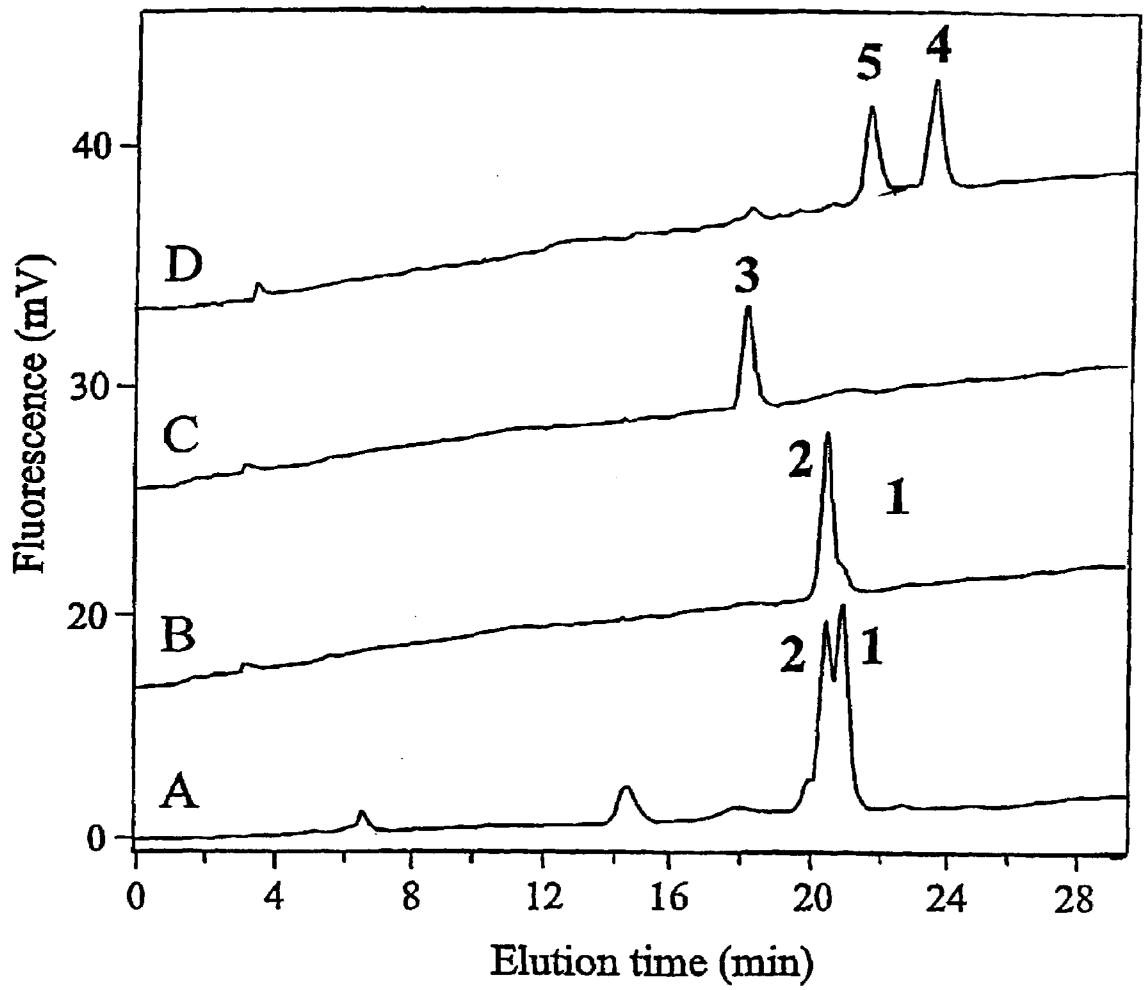

FIGS. 4*a*, 4*b* and 4*c* show the alignment of *A. thaliana* β1,2-xylosyltransferase cDNAs, one genomic DNA and one EST sequence;

FIG. 5 shows the alignment of amino acid sequences of β1,2-xylosyltransferase derived from the cDNAs, from a genomic DNA and from a EST sequence;

FIG. 6 is a schematic representation of the β1,2-xylosyltransferase as well as the PCR-products and the hydrophobicity of the amino acid residues;

FIG. 7 shows a comparison of the β1,2-xylosyltransferase activity of insect cells transfected with the β1,2-xylosyltransferase gene with that of a negative control;

FIGS. 8*a* and 8*b* shows the structure of the acceptor substrate and product of the β1,2-xylosyltransferase;

FIG. 9 shows mass spectra;

FIG. 10 shows the analysis of the β1,2-xylosyltransferase product by reversed-phase HPLC, and FIG. 11 shows the alignment of the predicted amino acid sequence derived from the cDNA of the present application with the amino acid sequence of the β1,2-xylosyltransferase purified from soybean.

EXAMPLE 1

RT-PCR and cDNA Cloning

Primers for the amplification of the putative β1,2-xylosyltransferase cDNA by RT-PCR were designed as follows: A BLASTP search of the DDBJ database using two soybean peptides (SEQ ID NO: 1 and 2; corresponding to SEQ ID NO: 3 and 5 in FIG. 4 in patent WO99/29835 A1; however, the C-terminal amino acids LG were omitted from SEQ ID NO: 5) (see FIG. 1) showed one protein sequence derived from a *Arabidopsis thaliana* genomic DNA sequence (Acc. Nr. AB015479) with more than 80 % homology (SEQ ID NO: 3). Primers 3 (SEQ ID NO: 4) and 4 (SEQ ID NO: 5) were based on the *A. thaliana* sequence homologous to the soybean peptides 2 and 3. Analysis of the homologous genomic DNA sequence using Gene-Finder at the BCM Search Launcher resulted in one predicted protein. Primer 1 (SEQ ID NO: 6) was designed to include the start codon of the predicted protein, whereas primer 2 (SEQ ID NO: 7) contains the stop codon of the predicted protein.

The entire RNA was isolated from young leaves of *Arabidopsis thaliana* var Columbia using the TRIzol reagent (Life Technologies). The RNA was treated with DNAse (Promega, RQl RNase Free DNase) to remove traces of genomic DNA. First-strand cDNA was synthesised from 1 μg of total RNA at 42° C. using oligo(dT) primers (Sigma) and AMV reverse transcriptase (Promega).

The first strand cDNA was subjected to a PCR, wherein different combinations of sense and antisense primers were used (illustrated in FIG. 6): The product of primer 3 and primer 4 was a DNA fragment with length of 174 bp (P1), the product of primer 1 and primer 2 was a 1605 bp (P2) DNA fragment, the product of primer 1 and primer 4 was a DNA fragment with length of 1525 bp (P3) and primer 3 and primer 4 produced a DNA of 254 bp (P4). For amplification of the putative open reading frame primer 1 and primer 2 were used. A PCR reaction contained in a total volume of 50 μl 0.2 μmol of each primer, 0.05 mM dNTPs, 2 mM $MgSO_4$, 20 mM Tris-HCl (pH 8.2 at 25° C.), 10 mM KCl, 10 mM $(NH_4)_2SO_4$, 0.1% Triton X-100, 5 μg nuclease-free BSA and 2.5 units Pfu DNA polymerase from Promega. After a first denaturing step at 94° C. for 2 min, 30 cycles of 1 min at 92° C., 40 sec at 53° C. and 3 min and 30 sec at 72° C. were performed. The last extension step was carried out at 72° C. for 8 min. PCR products were subcloned into SmaI linearised and dephosphorylated puc19 vector, and sequenced: The sequences of the subcloned fragments were obtained by means of the didesoxynucleotide method (ABI PRISM Dye Termination Cycle Sequencing Ready reaction Kit and ABI PRISM 310 Genetic analyzer from Perkin Elmer). As a result of the RT-PCR three slightly different cDNA sequences were obtained. The sequence of cDNA 6 which has a size of 1605 bp (xt-Ath6; SEQ ID NO: 8) and codes for a protein of 534 amino acids having a molecular weight of 60.2 kDA and a theoretical pI value of 7.52 (see FIG. 3) is identical to the nucleotide sequence derived from the genomic clone after removing of two introns (xt-Athgen.seq). cDNA 9 shows 4 base pair changes compared to cDNA 6, whereas cDNA 16 shows 6 base pair changes compared to cDNA 6 (illustrated in FIGS. 4*a*, 4*b* and 4*c*). Therefore the amino acid sequence derived from cDNA 9 comprises two changes compared to the amino acid sequence derived from cDNA 6 (SEQ ID NO: 8), and the amino acid sequence of cDNA 16 shows four changed residues (illustrated in FIG. 5).

FIG. 3 shows the cDNA-derived amino acid sequence (SEQ ID NO: 9) of the β1,2-xylosyltransferase (xt-Ath6; SEQ ID NO: 8). Potential sites for the asparagine-bound glycosylation are at Asn51, Asn301 and Asn479.

FIGS. 4*a*, 4*b* and 4*c* show the alignment of β1,2-xylosyltransferase nucleotide sequences from the *A. thaliana* cDNA 6 (xt-Ath6; SEQ ID NO: 8), the *A. thaliana* cDNA 9 (xt-Ath9), the *A. thaliana* cDNA 16 (xt-Ath16), the *A. thaliana* genomic DNA sequence after removing of two introns (xt-Athgen), and from a *A. thaliana* EST sequence (xtAthEST). The dotted line stands for the consensus sequence; the dashed line for a gap.

The genomic sequence (xt-Athgen; Acc. No. AB015479, start codon at position 58185–58187, stop codon at position 60214–60216 of the genomic DNA) results from removing of two putative introns (intron 1: from position 58881 to 59116 of the genomic DNA; intron 2: from position 59268 to 59458 of the genomic DNA) using the splice site prediction server NetPlantGene. The *A. thaliana* EST sequence (xt-AthEST; Acc. No. AI994524) is the result of a database search using BLASTN.

FIG. 5 shows the alignment of amino acid sequences from β1,2-xylosyltransferase derived from *A. thaliana* cDNA 6 (xt-Ath6; SEQ ID NO: 9), from *A. thaliana* cDNA 9 (xt-Ath9), from *A. thaliana* cDNA 16 (xt-Ath16), from the *A. thaliana* genomic sequence (xt-Athgen), and derived from a *A. thaliana* EST sequence (xt-AthEST). The dotted line stands for a consensus sequence; the dashed line stands for a gap.

In FIG. 6, the schematic predicted β1,2-xylosyltransferase protein (top) and the derived hydrophobicity index using ProtScale, of the encoded protein (bottom) are illustrated, a positive hydrophobicity index meaning an increased hydrophobicity. Therebetween the sizes of the four above-indicated PCR products (P1–P4) are shown in relationship to the cDNA. "C" coding for the postulated cytoplasmic region, "T" for the postulated transmembrane region, and "G" for the postulated Golgi lumen catalytic region of the transferase. The analysis of the protein sequence by "TMpred" (from EMBnet,) gave an assumed transmembrane region from Ile11 to Phe29. The C-terminal region of the enzyme probably comprises the catalytic region and consequently should point into the lumen of the Golgi apparatus. According to this, this transferase seems to be a type II transmembrane protein like all the hitherto analysed glycosyltransferases which are involved in glycoprotein biosynthesis (Joziasse, 1992, Glycobiology 2, 271–277). The grey regions represent the position of the two peptides, the hexagons represent the potential N-glycosylation sites. A BLAST search in data banks accessible via NCBI showed only high homology to one other plant sequence (hybrid aspen, Acc. No. AI62640).

EXAMPLE 2

Expression of Recombinant β1,2-xylosyltransferase in Insect Cells

The entire coding region of the assumed β1,2-xylosyltransferase including cytoplasmatic and transmembrane region was removed from the puc19 vector by BamHI and ECORI digestion and subcloned into BamHI/EcoRI digested and dephosphorylated baculovirus transfer vector pVL 1393 (PharMingen, San Diego, Calif.). Correct cloning was confirmed by sequencing using pVL1393 forward primer 5'-AACCATCTCGCAAATAAATAAGTA-3' (SEQ ID NO: 10) and pVL1393 reverse primer 5'-GTCGGGTTTAACATTACGGATTTC-3' (SEQ ID NO: 11). To ensure a homologous recombination, 1 μg of the transfer vector was co-transfected with 200 ng linear Baculo-Gold viral DNA (PharMingen, San Diego, Calif.) into $1\times10^6$ Sf-9 cells in IPL-41 Medium using Lipofectin (Life Technologies) according to the manufacturer's protocol. After an incubation of 5 days at 27° C., various volumes of the supernatant with the recombinant virus were used for infection of Sf-21 insect cells. Cells were incubated in IPL-41 medium supplemented with 5% heat-inactivated fetal calf serum for 4 days at 27° C., then harvested and washed 2× with phosphate-buffered saline solution. The cells were resuspended and homogenised in the following buffer (1 ml per $10^7$ cells): 100 mM MES buffer, pH 7.0, with 1% Triton X-100, 1 mM DTT, 1 mM PMSF, 5 μg/ml Leupeptin (Sigma), 5 μg/ml E-64 (Serva) and incubated on ice for 30 min.

EXAMPLE 3

Assay for β1,2-xylosyltransferase Activity

The cell homogenates were assayed for β1,2-xylosyltransferase activity. Negative controls were carried out with the same number of uninfected cells. The assay mixtures contained, in a total volume of 20 μl, 13 μl of homogenised cells, 2 nmol dabsylated GnGn hexapeptide or GnGn-pyridylamine as acceptor substrate (FIG. 8*a*), 1 mM UDP-xylose as donor substrate, 10 mM ATP, 20 mM MnCl2 and 1 mM 2-acetamido-1,2-dideoxy-nojirimycin was included to prevent degradation of product by N-acetylhexosaminidase. The samples were incubated for 1 hour at 37° C. and analysed by MALDI-TOF mass spectrometry.

FIG. 7 shows the measured enzyme activity of the recombinant β1,2-xylosyltransferase as well as of the negative control. Grey bars show the activity when GnGn hexapeptide was used as a substrate, whereas black bars indicate the use of GnGn-pyridylamin as a substrate. The enzyme activity of the cotransfected cells was 30× higher than that of the negative controls.

The structure of the acceptor substrate of β1,2-xylosyltransferase is shown in FIG. 8*a*, and the postulated product in FIG. 8*b*, where R represents either a pyridylamine or dabsylated hexapeptide residue.

EXAMPLE 4

Mass Spectrometry of the xylosyltransferase Product

Mass spectrometry was performed on a DYNAMO (BioAnalysis, Santa Fe, N. Mex.), a MALDITOF MS which is capable of dynamic extraction (synonym for late extraction). Two types of sample matrix preparations were used: dabsylated glycopeptides were dissolved in 5% formic acid, and aliquots were applied to the target, air-dried, and covered with 1% alpha-cyano-4-hydroxy cinnamic acid. Pyridylaminated glycans were diluted with water, applied to the target and air-dried. After addition of 2% 2.5-dihydroxy benzoic acid, the samples were immediately dried by applying vacuum.

FIG. 9 shows the mass spectrum of these samples, (A) being the negative control: The main peak (S) shows the dabsyl-Val-Gly-Glu-($GlcNAc_4Man_3$)Asn-Arg-Thr substrate, the calculated $[M+H]^+$ value being 2262.3. This substrate also appears as sodium addition product and as smaller ion which has been formed by fragmentation of the Azo function of the dabsyl group, at (S*). The peak at m/z=2424.4 shows the incomplete de-galactosylation of the substrate. The mass spectrum (B) shows the sample with recombinant β1,2-xylosyltransferase after incubation for 1 h at 37° C. The main peak (P), having a $[M+H]^+$ value of 2393.4, represents the xylosylated product.

EXAMPLE 5

HPLC-Analysis of the xylosyltransferase Product

Xylosyltransferase assays were performed as described above under example 3 except that 10 nmol of GnGn-pyridylamine were used as the acceptor substrate. After 4 h of incubation the sample was analyzed both by MALDI-TOF mass spectrometry and by rever sed-phase HPLC to verify the structure of the product. The presumed product peak eluting slightly ahead of the substrate GnGn-PA was collected. By MALDI-TOF MS the product's mass was determined to be 1550.9 which is in good agreement with being GnGnX-PA. Upon digestion with β-N-acetylglucosaminidase from bovine kidney (in 50 mM sodium citrate buffer of pH 5.0 for 20 h at 37° C. with 25 mU of enzyme), the glycan eluted with about the retention of MM. This is in keeping with published data on the retention of MM-PA and MMX-PA (Wilson & Altmann, 1998, Glycoconj. J. 15, 1055–1070). Further digestion with alpha-mannosidase from jack beans under the chosen conditions (20 h at 37° C. with 50 mU of enzyme) resulted in the appearance of two new peaks. As the alpha-1,3-linked mannose is considerably more sensitive to mannosidase than the alpha-1,6-linked mannose, the peaks are assigned to 00X and M0X (in the order of elution). Indeed, M0X-pyridylamine prepared from bromelain by defucosylation with acid coeluted with the presumed M0X derived from the xylosyltransferase product. The fairly high shift of elution time due to the removal of the alpha-1,3-linked mannose residue is a strong indication of the β-mannose being substituted by xylose (Wilson & Altmann, 1998, Glycoconj. J. 15, 1055–1070; Altmann, 1998, Glycoconj. J. 15, 79–82).

FIG. 10 shows the analysis of the xylosyltransferase product by reversed-phase HPLC. (A) transferase incubation mixture; (B) isolated xylosyltransferase product; (C) isolated xylosyltransferase product after digestion with β-N-acetylglucosaminidase; (D) isolated xylosyltransferase product after further digestion with alpha-mannosidase. The assignments of peaks are as follows: 1, GnGn-PA; 2, GnGnX-PA; 3, MMX-PA; 4, M0X-PA; 5, 00X-PAA; 6, M0-PA (from trace of substrate in isolated product). For abbreviations of N-glycan structures see Wilson I. B. H. and Altmann, F., 1998, Glycoconj. J. 15, 1055–1077.

FIG. 11 shows the alignment of the predicted amino acid sequence according to the WO 99/29835 A1. This alignment shows that the amino acid sequence of the purified soybean enzym corresponds only to amino acids 199–469 of the sequence derived from the cDNA according to the present invention. Furthermore, the predicted amino acid sequence derived from the cDNA of the present application contains two insertions (corresponding to aa 375–382 and aa 425–429 of the predicted sequence) compared to the sequence of the purified soybean enzyme.

The invention claimed is:

1. An isolated DNA molecule comprising:

(a) SEQ ID NO: 8 with an open reading frame from nucleotide 227 to nucleotide 1831, (b) a sequence that is at least 95% homologous with SEQ ID NO: 8, (c) a sequence that hybridizes with full complement of SEQ ID NO: 8 under stringent conditions of 7% sodium dodecyl sulfate (SDS), 0.5M $NaPO_4$, pH 7.0, 1mM EDTA at 50° C., and washed with 1% SDS at 42° C., or (d) a sequence which is degenerate to SEQ ID NO: 8 due to the genetic code, (e) The full compliment of DNA molecule in a, b, c or d, and wherein any of sequences (a) through (d) codes for a protein having β1,2-xylosyltransferase activity.

2. An isolated DNA molecule according to claim 1, wherein it comprises 1780 to 1880 nucleotides.

3. An isolated DNA molecule according to claim 1, covalently associated with a detectable marker substance.

4. An isolated DNA molecule according to claim 1, wherein said DNA sequence comprises a deletion, insertion and/or substitution mutation and further wherein said DNA molecule is at least 95% homologous with SEQ ID NO: 8.

5. A biologically functional vector, comprising a DNA molecule according to claim 1.

6. A biologically functional vector comprising a DNA molecule according to claim 1 and a promoter, wherein the polynucleotide is inversely orientated with respect to the promoter.

7. A biologically functional vector, comprising a DNA molecule according to claim 4.

8. A method of producing β1 ,2-xylosyltransferase, comprising transforming a vector with the DNA molecule according to claim 1, transfecting said vector into a host cell, and selecting and amplifying transfected host cell, wherein the host cell expresses active β1 ,2-xylosyltransferase.

9. An isolated DNA molecule according to claim 1, wherein said sequence is at least 95% identical to the sequence according to SEQ ID NO 8.

10. An isolated DNA molecule according to claim 1, comprising 1831 nucleotides.

* * * * *

SEQUENCE LISTING

```
<160> NUMBER OF SEQ ID NOS: 11

<210> SEQ ID NO 1
<211> LENGTH: 27
<212> TYPE: PRT
<213> ORGANISM: soyabean

<400> SEQUENCE: 1

Ser Gln Val Gln Ala Ile His Asp Ala Ser Val Ile Ile Gly Ala His
  1               5                  10                  15

Gly Ala Gly Leu Thr His Ile Val Ser Ala Leu
             20                  25
```

-continued

<210> SEQ ID NO 2
<211> LENGTH: 8
<212> TYPE: PRT
<213> ORGANISM: soyabean

<400> SEQUENCE: 2

```
Gly Leu Glu Tyr His Ala Ile Asn
  1               5
```

<210> SEQ ID NO 3
<211> LENGTH: 60
<212> TYPE: PRT
<213> ORGANISM: arabidopsis thaliana

<400> SEQUENCE: 3

```
Asp Gln Val Arg Ala Ile Gln Asp Ala Ser Val Ile Ile Gly Ala His
  1               5                  10                  15

Gly Ala Gly Leu Thr His Ile Val Ser Ala Thr Pro Asn Thr Thr Ile
             20                  25                  30

Phe Glu Ile Ile Ser Val Glu Phe Gln Arg Pro His Phe Glu Leu Ile
         35                  40                  45

Ala Lys Trp Lys Gly Leu Glu Tyr His Ala Met His
     50                  55                  60
```

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 4

```
gatcaagtcc gagccattca a                                              21
```

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 5

```
cgcgtgatac tccaatcctt t                                              21
```

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 6

```
atgagtaaac ggaatccgaa g                                              21
```

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 7

```
ttagcagcca aggctcttca t                                              21
```

-continued

<210> SEQ ID NO 8
<211> LENGTH: 1831
<212> TYPE: DNA
<213> ORGANISM: Arabidopsis thaliana

<400> SEQUENCE: 8
aaatctgcag actctcaaaa ttccgattca tcttattgaa gaacaatttt ccggcgaaac 60
agccgatgaa gtctcgcctg aatcttctgt acctttcacc ggcgattgac ttcacttcag 120
aatcgagaga gaagaaatcg atggaaaact aaaaatagaa agagtttcaa attctcgctc 180
tctcttcaaa accgcaaatc aagggaacga gagacgagag agagagatga gtaaacggaa 240
tccgaagatt ctgaagattt ttctgtatat gttacttctc aactctctct ttctcatcat 300
ctacttcgtt tttcactcat cgtcgttttc accggagcag tcacagcctc ctcatatata 360
ccacgtttca gtgaataacc aatcggcgat tcagaaaccg tggccgatct taccttctta 420
cctcccatgg acgccgccgc agaggaatct accaactggc tcctgcgaag gttacttcgg 480
gaatggattt acaaagagag ttgacttcct taagccgagg attggaggag gaggagaagg 540
aagctggttc cgatgttttt acagtgagac attacagagt tcgatttgtg aaggaaggaa 600
tctgagaatg gttccggatc ggattgttat gtcgagagga ggtgagaagt tagaggaagt 660
tatggggagg aaagaggagg aggagcttcc tgcgtttcga caaggtgcgt ttgaggtagc 720
ggaagaggtt tcttcacggt taggttttaa gagacaccgt cgttttggtg gaggagaagg 780
aggtagtgcg gtttctcggc ggctggtgaa tgatgagatg ttgaatgaat atatgcaaga 840
aggtggaatt gatagacata caatgagaga tttggttgct tcgattcgtg ctgttgatac 900
caatgatttc gtttgtgaag agtgggtgga ggaaccgacc ttgcttgtca ctagattcga 960
gtacgcaaat ctcttccata ctgtgacaga ttggtatagt gcctatgttt cgtctagagt 1020
caccggtttg cctaatcgac ctcacgttgt tttcgttgac ggacactgca cgacgcagct 1080
agaagaaaca tggacagctt tgttttccgg aatcagatac gcaaagaact tcaccaaacc 1140
ggtttgtttc cgccacgcga ttctttcacc attgggatac gaaaccgctc tttttaaagg 1200
cttgtccgga gaaatagact gcaagggaga ttcagctcac aatctgtggc aaaacccgga 1260
cgataaaagg actgcgagga tatcagagtt tggtgaaatg atcagagcag ctttcgggtt 1320
gcctgtcaat agacaccgct cattagaaaa gccgctatca tcatcatcat catcagcctc 1380
agtttataat gttctttttg tccgccgtga agattactta gcccatcctc gtcatggcgg 1440
taaagtccag tctcggctca tcaatgagga agaagtgttc gactcgttgc atcattgggt 1500
tgcaactggg tccaccggtc tgaccaaatg cgggattaac cttgtgaatg gcttgcttgc 1560
acacatgtca atgaaagatc aagtccgagc cattcaagat gcttcagtga tcataggagc 1620
tcatggagca ggactgactc acattgtctc tgcaacacca aacacaacga tatttgagat 1680
aataagcgtc gagtttcaga gacctcattt cgagcttata gctaagtgga aaggattgga 1740
gtatcacgcg atgcatctgg cgaactcacg agcggaacca acggctgtga ttgagaagtt 1800
aacggagatc atgaagagcc ttggctgcta a 1831

<210> SEQ ID NO 9
<211> LENGTH: 534
<212> TYPE: PRT
<213> ORGANISM: Arabidopsis thaliana

<400> SEQUENCE: 9

Met Ser Lys Arg Asn Pro Lys Ile Leu Lys Ile Phe Leu Tyr Met Leu
1 5 10 15

-continued

```
Leu Leu Asn Ser Leu Phe Leu Ile Ile Tyr Phe Val Phe His Ser Ser
            20                  25                  30

Ser Phe Ser Pro Glu Gln Ser Gln Pro Pro His Ile Tyr His Val Ser
        35                  40                  45

Val Asn Asn Gln Ser Ala Ile Gln Lys Pro Trp Pro Ile Leu Pro Ser
    50                  55                  60

Tyr Leu Pro Trp Thr Pro Pro Gln Arg Asn Leu Pro Thr Gly Ser Cys
65                  70                  75                  80

Glu Gly Tyr Phe Gly Asn Gly Phe Thr Lys Arg Val Asp Phe Leu Lys
                85                  90                  95

Pro Arg Ile Gly Gly Gly Gly Glu Gly Ser Trp Phe Arg Cys Phe Tyr
            100                 105                 110

Ser Glu Thr Leu Gln Ser Ser Ile Cys Glu Gly Arg Asn Leu Arg Met
        115                 120                 125

Val Pro Asp Arg Ile Val Met Ser Arg Gly Gly Glu Lys Leu Glu Glu
    130                 135                 140

Val Met Gly Arg Lys Glu Glu Glu Glu Leu Pro Ala Phe Arg Gln Gly
145                 150                 155                 160

Ala Phe Glu Val Ala Glu Glu Val Ser Ser Arg Leu Gly Phe Lys Arg
                165                 170                 175

His Arg Arg Phe Gly Gly Gly Glu Gly Gly Ser Ala Val Ser Arg Arg
            180                 185                 190

Leu Val Asn Asp Glu Met Leu Asn Glu Tyr Met Gln Glu Gly Gly Ile
        195                 200                 205

Asp Arg His Thr Met Arg Asp Leu Val Ala Ser Ile Arg Ala Val Asp
    210                 215                 220

Thr Asn Asp Phe Val Cys Glu Glu Trp Val Glu Glu Pro Thr Leu Leu
225                 230                 235                 240

Val Thr Arg Phe Glu Tyr Ala Asn Leu Phe His Thr Val Thr Asp Trp
                245                 250                 255

Tyr Ser Ala Tyr Val Ser Ser Arg Val Thr Gly Leu Pro Asn Arg Pro
            260                 265                 270

His Val Val Phe Val Asp Gly His Cys Thr Thr Gln Leu Glu Glu Thr
        275                 280                 285

Trp Thr Ala Leu Phe Ser Gly Ile Arg Tyr Ala Lys Asn Phe Thr Lys
    290                 295                 300

Pro Val Cys Phe Arg His Ala Ile Leu Ser Pro Leu Gly Tyr Glu Thr
305                 310                 315                 320

Ala Leu Phe Lys Gly Leu Ser Gly Glu Ile Asp Cys Lys Gly Asp Ser
                325                 330                 335

Ala His Asn Leu Trp Gln Asn Pro Asp Asp Lys Arg Thr Ala Arg Ile
            340                 345                 350

Ser Glu Phe Gly Glu Met Ile Arg Ala Ala Phe Gly Leu Pro Val Asn
        355                 360                 365

Arg His Arg Ser Leu Glu Lys Pro Leu Ser Ser Ser Ser Ser Ser Ala
    370                 375                 380

Ser Val Tyr Asn Val Leu Phe Val Arg Arg Glu Asp Tyr Leu Ala His
385                 390                 395                 400

Pro Arg His Gly Gly Lys Val Gln Ser Arg Leu Ile Asn Glu Glu Glu
                405                 410                 415

Val Phe Asp Ser Leu His His Trp Val Ala Thr Gly Ser Thr Gly Leu
            420                 425                 430
```

-continued

```
Thr Lys Cys Gly Ile Asn Leu Val Asn Gly Leu Leu Ala His Met Ser
        435                 440                 445

Met Lys Asp Gln Val Arg Ala Ile Gln Asp Ala Ser Val Ile Ile Gly
    450                 455                 460

Ala His Gly Ala Gly Leu Thr His Ile Val Ser Ala Thr Pro Asn Thr
465                 470                 475                 480

Thr Ile Phe Glu Ile Ile Ser Val Glu Phe Gln Arg Pro His Phe Glu
                485                 490                 495

Leu Ile Ala Lys Trp Lys Gly Leu Glu Tyr His Ala Met His Leu Ala
            500                 505                 510

Asn Ser Arg Ala Glu Pro Thr Ala Val Ile Glu Lys Leu Thr Glu Ile
        515                 520                 525

Met Lys Ser Leu Gly Cys
    530


<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 10

aaccatctcg caaataaata agta                                         24


<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 11

gtcgggttta acattacgga tttc                                         24
```